United States Patent
Zhang et al.

(10) Patent No.: US 11,090,017 B2
(45) Date of Patent: Aug. 17, 2021

(54) GENERATING SYNTHESIZED PROJECTION IMAGES FOR 3D BREAST TOMOSYNTHESIS OR MULTI-MODE X-RAY BREAST IMAGING

(71) Applicant: Hologic, Inc., Marlborough, MA (US)

(72) Inventors: Yiheng Zhang, Reading, MA (US); Zhenxue Jing, Southbury, CT (US); Christopher Ruth, Boxford, MA (US)

(73) Assignee: Hologic, Inc., Marlborough, MA (US)

( * ) Notice: Subject to any disclaimer, the term of this patent is extended or adjusted under 35 U.S.C. 154(b) by 103 days.

(21) Appl. No.: 16/567,910

(22) Filed: Sep. 11, 2019

(65) Prior Publication Data
US 2020/0085393 A1     Mar. 19, 2020

Related U.S. Application Data

(60) Provisional application No. 62/730,818, filed on Sep. 13, 2018.

(51) Int. Cl.
*A61B 6/00* (2006.01)
*A61B 6/04* (2006.01)
(Continued)

(52) U.S. Cl.
CPC .......... *A61B 6/502* (2013.01); *A61B 5/7267* (2013.01); *A61B 6/025* (2013.01); *A61B 6/4028* (2013.01);
(Continued)

(58) Field of Classification Search
CPC ....... A61B 5/7267; A61B 6/025; A61B 6/032; A61B 6/4028; A61B 65/02; A61B 6/5235;
(Continued)

(56) References Cited

U.S. PATENT DOCUMENTS 3,365,575 A   1/1968  Strax
3,502,878 A   3/1970  Stewart
(Continued)

FOREIGN PATENT DOCUMENTS

CN    102222594    10/2011
DE    102004051401    5/2006
(Continued)

OTHER PUBLICATIONS

Kachelriess, Marc et al., "Flying Focal Spot (FFS) in Cone-Beam CT", 2004 IEEE Nuclear Science Symposium Conference Record, Oct. 16-22, 2004, Rome Italy, vol. 6, pp. 3759-3763.
(Continued)

*Primary Examiner* — Irakli Kiknadze
(74) *Attorney, Agent, or Firm* — Merchant & Gould P.C.

(57) ABSTRACT

Methods and systems for medical imaging including synthesizing virtual projections from acquired real projections and generating reconstruction models and images based on the synthesized virtual projections and acquired real projections. For example, first x-ray imaging data is generated from a detected first x-ray emission at a first angular location and second x-ray imaging data is generated from a detected second x-ray emission at a second angular location. Based on at least the first x-ray imaging data and the second x-ray imaging data, third x-ray imaging data for a third angular location relative to the breast may be synthesized. An image of the breast may be displayed or generated from the third x-ray imaging data.

19 Claims, 13 Drawing Sheets

(51) Int. Cl.
*G06T 11/00* (2006.01)
*G06T 7/70* (2017.01)
*G06T 7/00* (2017.01)
*A61B 5/00* (2006.01)
*A61B 6/02* (2006.01)
*G06T 5/50* (2006.01)

(52) U.S. Cl.
CPC .............. *A61B 6/5235* (2013.01); *G06T 5/50* (2013.01); *G06T 7/0012* (2013.01); *G06T 7/70* (2017.01); *G06T 11/003* (2013.01); *G06T 2207/10081* (2013.01); *G06T 2207/10112* (2013.01); *G06T 2207/20081* (2013.01); *G06T 2207/20084* (2013.01); *G06T 2207/20221* (2013.01); *G06T 2207/30068* (2013.01); *G06T 2207/30168* (2013.01)

(58) Field of Classification Search
CPC ... A61B 6/54; A61B 6/502; A61B 2090/3908; A61B 2090/3966; A61B 2576/02; A61B 5/4312; A61B 6/5258; A61B 8/0825; A61B 6/4014; A61B 6/4085; A61B 6/488; A61B 6/4452; A61B 6/06; A61B 6/463; A61B 5/0035; A61B 5/0059; A61B 5/055; A61B 6/4435; A61B 6/027; A61B 6/461; A61B 17/15; A61B 17/155; A61B 17/157; A61B 17/1666; A61B 2503/06; A61B 5/0004; A61B 5/0022; A61B 5/1451; A61B 5/14532; A61B 5/4839; A61B 5/746; A61B 6/5205; G06T 11/003; G06T 11/006; G06T 2207/10081; G06T 2207/10112; G06T 2207/20081; G06T 2207/20084; G06T 2207/20221; G06T 2207/30068; G06T 2207/30168; G06T 5/50; G06T 7/0012; G06T 7/70; G06T 11/008; G06T 2207/1112; G06T 2211/436; G06T 19/20; G06T 2210/41; G06T 2211/412; G06T 19/00; G06T 2219/2008; G06T 11/60; G06T 2207/30204; G06T 15/08; G06T 7/0014; G06T 2219/028; A61N 5/1049; A61N 2005/1061; A61N 5/1067; A61N 5/1015; A61N 2005/1062; A61N 5/10; A61N 5/1048; A61N 5/1081; A61N 5/1082; A61N 2005/1018; A61N 2005/1092; A61N 5/1037; A61N 5/1039; A61N 5/1042; A61N 5/1065; A61N 2005/1003; A61N 2005/1004; A61N 2005/1024; A61N 5/1083; G01N 2223/308; G01N 23/046; G01N 2223/401; G01N 2223/639; G01N 23/04; G01N 2223/419; G01N 24/08; G01V 5/0016; G01V 5/0083; G01V 5/0008; G06K 2209/053; G06K 9/4638; G06K 9/6201; G06K 9/00771; G06K 9/4604; G06K 9/4671; G06K 9/6211; G06K 9/6267; G06K 9/2054; G06K 9/6202; A61M 2025/0004; A61M 2025/0681; A61M 25/0021; A61M 25/0105; A61M 25/0133; A61M 25/0136; A61M 25/0147; A61M 25/10; A61M 2025/004; A61M 25/0029; A61M 2025/0037; A61M 25/0026; A61M 25/0097; A61M 25/01; A61M 25/0102; A61M 25/0108; A61M 25/0169; A61M 25/04; H05K 999/99; G01T 1/00; H04N 13/275; G06N 3/02; G06N 5/04; G21K 1/02; G21K 1/025; H01J 2235/062; H01J 2235/068; H05G 1/70
USPC ......................................... 378/19, 21, 62, 37
See application file for complete search history.

(56) References Cited

U.S. PATENT DOCUMENTS

| | | |
|---|---|---|
| 3,863,073 A | 1/1975 | Wagner |
| 3,971,950 A | 7/1976 | Evans et al. |
| 4,160,906 A | 7/1979 | Daniels et al. |
| 4,310,766 A | 1/1982 | Finkenzeller et al. |
| 4,380,086 A | 4/1983 | Vagi |
| 4,496,557 A | 1/1985 | Malen et al. |
| 4,513,433 A | 4/1985 | Weiss et al. |
| 4,542,521 A | 9/1985 | Hahn et al. |
| 4,559,641 A | 12/1985 | Caugant et al. |
| 4,662,379 A | 5/1987 | Macovski |
| 4,706,269 A | 11/1987 | Reina et al. |
| 4,721,856 A | 1/1988 | Saotome et al. |
| 4,744,099 A | 5/1988 | Huettenrauch et al. |
| 4,752,948 A | 6/1988 | MacMahon |
| 4,760,589 A | 7/1988 | Siczek |
| 4,763,343 A | 8/1988 | Yanaki |
| 4,773,086 A | 9/1988 | Fujita et al. |
| 4,773,087 A | 9/1988 | Plewes |
| 4,819,258 A | 4/1989 | Kleinman et al. |
| 4,821,727 A | 4/1989 | Levene et al. |
| 4,969,174 A | 11/1990 | Scheid et al. |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,163,075 A | 11/1992 | Lubinsky et al. |
| 5,164,976 A | 11/1992 | Scheid et al. |
| 5,199,056 A | 3/1993 | Darrah |
| 5,212,637 A | 5/1993 | Saxena |
| 5,240,011 A | 8/1993 | Assa |
| 5,256,370 A | 10/1993 | Slattery et al. |
| 5,274,690 A | 12/1993 | Burke |
| 5,289,520 A | 2/1994 | Pellegrino et al. |
| 5,291,539 A | 3/1994 | Thumann et al. |
| 5,313,510 A | 5/1994 | Ebersberger |
| 5,359,637 A | 10/1994 | Webber |
| 5,365,562 A | 11/1994 | Toker |
| 5,415,169 A | 5/1995 | Siczek et al. |
| 5,426,685 A | 6/1995 | Pellegrino et al. |
| 5,452,367 A | 9/1995 | Bick et al. |
| 5,506,877 A | 4/1996 | Niklason et al. |
| 5,526,394 A | 6/1996 | Siczek et al. |
| 5,528,658 A | 6/1996 | Hell |
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzki et al. |
| 5,609,152 A | 3/1997 | Pellegrino et al. |
| 5,627,869 A | 5/1997 | Andrew et al. |
| 5,657,362 A | 8/1997 | Giger et al. |
| 5,668,844 A | 9/1997 | Webber |
| 5,668,889 A | 9/1997 | Hara |
| 5,706,327 A | 1/1998 | Adamkowski et al. |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,841,829 A | 11/1998 | Dolazza |
| 5,844,965 A | 12/1998 | Galkin |
| 5,864,146 A | 1/1999 | Karellas |
| 5,872,828 A | 2/1999 | Niklason et al. |
| 5,878,104 A | 3/1999 | Ploetz |

(56) References Cited

U.S. PATENT DOCUMENTS

| | | |
|---|---|---|
| 5,896,437 A | 4/1999 | Ploetz |
| 5,941,832 A | 8/1999 | Tumey et al. |
| 5,970,118 A | 10/1999 | Sokolov |
| 5,986,662 A | 11/1999 | Argiro et al. |
| 5,999,836 A | 12/1999 | Nelson et al. |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers et al. |
| 6,137,527 A | 10/2000 | Abdel-Malek et al. |
| 6,141,398 A | 10/2000 | He et al. |
| 6,149,301 A | 11/2000 | Kautzer et al. |
| 6,167,115 A | 12/2000 | Inoue |
| 6,175,117 B1 | 1/2001 | Komardin et al. |
| 6,196,715 B1 | 3/2001 | Nambu et al. |
| 6,207,958 B1 | 3/2001 | Giakos |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,244,507 B1 | 6/2001 | Garland |
| 6,256,369 B1 | 7/2001 | Lai |
| 6,256,370 B1 | 7/2001 | Yavuz |
| 6,272,207 B1 | 8/2001 | Tang |
| 6,289,235 B1 | 9/2001 | Webber et al. |
| 6,292,530 B1 | 9/2001 | Yavus et al. |
| 6,327,336 B1 | 12/2001 | Gingold et al. |
| 6,341,156 B1 | 1/2002 | Baetz et al. |
| 6,345,194 B1 | 2/2002 | Nelson et al. |
| 6,375,352 B1 | 4/2002 | Hewes et al. |
| 6,411,836 B1 | 6/2002 | Patel et al. |
| 6,415,015 B2 | 7/2002 | Nicolas et al. |
| 6,418,189 B1 | 7/2002 | Schafer |
| 6,442,288 B1 | 8/2002 | Haerer et al. |
| 6,459,925 B1 | 10/2002 | Nields et al. |
| 6,480,565 B1 | 11/2002 | Ning |
| 6,490,476 B1 | 12/2002 | Townsend et al. |
| 6,501,819 B2 | 12/2002 | Unger et al. |
| 6,542,575 B1 | 4/2003 | Schubert |
| 6,553,096 B1 | 4/2003 | Zhou et al. |
| 6,556,655 B1 | 4/2003 | Chichereau et al. |
| 6,574,304 B1 | 6/2003 | Hsieh et al. |
| 6,574,629 B1 | 6/2003 | Cooke, Jr. et al. |
| 6,597,762 B1 | 7/2003 | Ferrant et al. |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Gemperline et al. |
| 6,638,235 B2 | 10/2003 | Miller et al. |
| 6,647,092 B2 | 11/2003 | Eberhard et al. |
| 6,744,848 B2 | 6/2004 | Stanton et al. |
| 6,748,044 B2 | 6/2004 | Sabol et al. |
| 6,751,285 B2 | 6/2004 | Eberhard et al. |
| 6,758,824 B1 | 7/2004 | Miller et al. |
| 6,813,334 B2 | 11/2004 | Koppe et al. |
| 6,882,700 B2 | 4/2005 | Wang et al. |
| 6,885,724 B2 | 4/2005 | Li et al. |
| 6,895,076 B2 | 5/2005 | Halsmer |
| 6,909,790 B2 | 6/2005 | Tumey et al. |
| 6,909,792 B1 | 6/2005 | Carrott et al. |
| 6,912,319 B1 | 6/2005 | Barnes et al. |
| 6,940,943 B2 | 9/2005 | Claus et al. |
| 6,950,493 B2 | 9/2005 | Besson |
| 6,957,099 B1 | 10/2005 | Arnone et al. |
| 6,970,531 B2 | 11/2005 | Eberhard et al. |
| 6,978,040 B2 | 12/2005 | Berestov |
| 6,987,831 B2 | 1/2006 | Ning |
| 6,999,554 B2 | 2/2006 | Mertelmeier |
| 7,001,071 B2 | 2/2006 | Deuringer |
| 7,016,461 B2 | 3/2006 | Rotondo |
| 7,110,490 B2 | 9/2006 | Eberhard et al. |
| 7,110,502 B2 | 9/2006 | Tsuji |
| 7,116,749 B2 | 10/2006 | Besson |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,190,758 B2 | 3/2007 | Hagiwara |
| 7,206,462 B1 | 4/2007 | Betke |
| 7,244,063 B2 | 7/2007 | Eberhard |
| 7,245,694 B2 | 7/2007 | Jing et al. |
| 7,286,645 B2 | 10/2007 | Freudenberger |
| 7,302,031 B2 | 11/2007 | Hjarn et al. |
| 7,315,607 B2 | 1/2008 | Ramsauer |
| 7,319,735 B2 | 1/2008 | Defreitas et al. |
| 7,319,736 B2 | 1/2008 | Rotondo |
| 7,323,692 B2 | 1/2008 | Rowlands et al. |
| 7,331,264 B2 | 2/2008 | Ozawa |
| 7,430,272 B2 | 9/2008 | Jing et al. |
| 7,443,949 B2 | 10/2008 | Defreitas et al. |
| 7,577,282 B2 | 8/2009 | Gkanatsios et al. |
| 7,583,786 B2 | 9/2009 | Jing et al. |
| 7,609,806 B2 | 10/2009 | Defreitas et al. |
| 7,616,731 B2 | 11/2009 | Pack |
| 7,616,801 B2 | 11/2009 | Gkanatsios et al. |
| 7,630,531 B2 | 12/2009 | Chui |
| 7,630,533 B2 | 12/2009 | Ruth et al. |
| 7,688,940 B2 | 3/2010 | Defreitas et al. |
| 7,697,660 B2 | 4/2010 | Ning |
| 7,702,142 B2 | 4/2010 | Ren et al. |
| 7,760,853 B2 | 7/2010 | Jing et al. |
| 7,760,924 B2 | 7/2010 | Ruth et al. |
| 7,792,245 B2 | 9/2010 | Hitzke et al. |
| 7,831,296 B2 | 11/2010 | Defreitas et al. |
| 7,839,979 B2 | 11/2010 | Hauttmann |
| 7,869,563 B2 | 1/2011 | Defreitas et al. |
| 7,881,428 B2 | 2/2011 | Jing et al. |
| 7,885,384 B2 | 2/2011 | Mannar |
| 7,894,646 B2 | 2/2011 | Shirahata et al. |
| 7,916,915 B2 | 3/2011 | Gkanatsios et al. |
| 7,949,091 B2 | 5/2011 | Jing et al. |
| 7,986,765 B2 | 7/2011 | Defreitas et al. |
| 7,991,106 B2 | 8/2011 | Ren et al. |
| 8,031,834 B2 | 10/2011 | Ludwig |
| 8,131,049 B2 | 3/2012 | Ruth et al. |
| 8,155,421 B2 | 4/2012 | Ren et al. |
| 8,170,320 B2 | 5/2012 | Smith et al. |
| 8,175,219 B2 | 5/2012 | Defreitas et al. |
| 8,285,020 B2 | 10/2012 | Gkanatsios et al. |
| 8,416,915 B2 | 4/2013 | Jing et al. |
| 8,452,379 B2 | 5/2013 | DeFreitas et al. |
| 8,457,282 B2 | 6/2013 | Baorui et al. |
| 8,515,005 B2 | 8/2013 | Ren et al. |
| 8,559,595 B2 | 10/2013 | Defreitas et al. |
| 8,565,372 B2 | 10/2013 | Stein et al. |
| 8,565,374 B2 | 10/2013 | DeFreitas et al. |
| 8,565,860 B2 | 10/2013 | Kimchy |
| 8,571,289 B2 | 10/2013 | Ruth et al. |
| 8,712,127 B2 | 4/2014 | Ren et al. |
| 8,767,911 B2 | 7/2014 | Ren et al. |
| 8,787,522 B2 | 7/2014 | Smith et al. |
| 8,831,171 B2 | 9/2014 | Jing et al. |
| 8,853,635 B2 | 10/2014 | O'Connor |
| 8,873,716 B2 | 10/2014 | Ren et al. |
| 9,042,612 B2 | 5/2015 | Gkanatsios et al. |
| 9,066,706 B2 | 6/2015 | Defreitas et al. |
| 9,226,721 B2 | 1/2016 | Ren et al. |
| 9,460,508 B2 | 10/2016 | Gkanatsios et al. |
| 9,498,175 B2 | 11/2016 | Stein et al. |
| 9,502,148 B2 | 11/2016 | Ren |
| 9,549,709 B2 | 1/2017 | DeFreitas et al. |
| 9,851,888 B2 | 12/2017 | Gkanatsios et al. |
| 9,895,115 B2 | 2/2018 | Ren |
| 10,108,329 B2 | 10/2018 | Gkanatsios et al. |
| 10,194,875 B2 | 2/2019 | DeFreitas et al. |
| 10,296,199 B2 | 5/2019 | Gkanatsios |
| 10,413,255 B2 | 9/2019 | Stein |
| 10,719,223 B2 | 7/2020 | Gkanatsios |
| 2001/0038681 A1 | 11/2001 | Stanton et al. |
| 2002/0012450 A1 | 1/2002 | Tsujii |
| 2002/0048343 A1 | 4/2002 | Launay et al. |
| 2002/0050986 A1 | 5/2002 | Inoue et al. |
| 2002/0070970 A1 | 6/2002 | Wood et al. |
| 2002/0075997 A1 | 6/2002 | Unger et al. |
| 2002/0090055 A1 | 7/2002 | Zur et al. |

(56) References Cited

U.S. PATENT DOCUMENTS

| | | |
|---|---|---|
| 2002/0094062 A1 | 7/2002 | Dolazza |
| 2002/0122533 A1 | 9/2002 | Marie et al. |
| 2002/0126798 A1 | 9/2002 | Harris |
| 2003/0007598 A1 | 1/2003 | Wang et al. |
| 2003/0010923 A1 | 1/2003 | Zur |
| 2003/0018272 A1 | 1/2003 | Treado et al. |
| 2003/0026386 A1 | 2/2003 | Tang et al. |
| 2003/0058989 A1 | 3/2003 | Rotondo |
| 2003/0072409 A1 | 4/2003 | Kaufhold et al. |
| 2003/0072417 A1 | 4/2003 | Kaufhold et al. |
| 2003/0073895 A1 | 4/2003 | Nields et al. |
| 2003/0095624 A1 | 5/2003 | Eberhard et al. |
| 2003/0097055 A1 | 5/2003 | Yanof et al. |
| 2003/0149364 A1 | 8/2003 | Kapur |
| 2003/0169847 A1 | 9/2003 | Karellas et al. |
| 2003/0194050 A1 | 10/2003 | Eberhard |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0212327 A1 | 11/2003 | Wang et al. |
| 2003/0215120 A1 | 11/2003 | Uppaluri et al. |
| 2004/0008809 A1 | 1/2004 | Webber |
| 2004/0066882 A1 | 4/2004 | Eberhard et al. |
| 2004/0066884 A1 | 4/2004 | Hermann Claus et al. |
| 2004/0066904 A1 | 4/2004 | Eberhard et al. |
| 2004/0070582 A1 | 4/2004 | Smith et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0146221 A1 | 7/2004 | Siegel et al. |
| 2004/0171986 A1 | 9/2004 | Tremaglio, Jr. et al. |
| 2004/0190682 A1 | 9/2004 | Deuringer |
| 2004/0213378 A1 | 10/2004 | Zhou et al. |
| 2004/0247081 A1 | 12/2004 | Halsmer |
| 2004/0264627 A1 | 12/2004 | Besson |
| 2004/0267157 A1 | 12/2004 | Miller et al. |
| 2005/0025278 A1 | 2/2005 | Hagiwara |
| 2005/0049521 A1 | 3/2005 | Miller et al. |
| 2005/0063509 A1 | 3/2005 | DeFreitas et al. |
| 2005/0078797 A1 | 4/2005 | Danielsson et al. |
| 2005/0089205 A1 | 4/2005 | Kapur |
| 2005/0105679 A1 | 5/2005 | Wu et al. |
| 2005/0113681 A1 | 5/2005 | DeFreitas et al. |
| 2005/0113715 A1 | 5/2005 | Schwindt et al. |
| 2005/0117694 A1 | 6/2005 | Francke |
| 2005/0129172 A1 | 6/2005 | Mertelmeier |
| 2005/0133706 A1 | 6/2005 | Eberhard |
| 2005/0135555 A1 | 6/2005 | Claus et al. |
| 2005/0135664 A1 | 6/2005 | Kaufhold et al. |
| 2005/0226375 A1 | 10/2005 | Eberhard et al. |
| 2005/0248347 A1 | 11/2005 | Damadian |
| 2006/0030784 A1 | 2/2006 | Miller et al. |
| 2006/0034426 A1 | 2/2006 | Freudenberger |
| 2006/0074288 A1 | 4/2006 | Kelly et al. |
| 2006/0098855 A1 | 5/2006 | Gkanatsios et al. |
| 2006/0109951 A1 | 5/2006 | Popescu |
| 2006/0126780 A1 | 6/2006 | Rotondo |
| 2006/0129062 A1 | 6/2006 | Nicoson et al. |
| 2006/0155209 A1 | 7/2006 | Miller et al. |
| 2006/0210016 A1 | 9/2006 | Francke |
| 2006/0262898 A1 | 11/2006 | Partain |
| 2006/0269041 A1 | 11/2006 | Mertelmeier |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0076844 A1 | 4/2007 | Defreitas et al. |
| 2007/0078335 A1 | 4/2007 | Horn |
| 2007/0140419 A1 | 6/2007 | Souchay |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0045833 A1 | 2/2008 | Defreitas et al. |
| 2008/0056436 A1 | 3/2008 | Pack |
| 2008/0101537 A1 | 5/2008 | Sendai |
| 2008/0112534 A1 | 5/2008 | Defreitas et al. |
| 2008/0118023 A1 | 5/2008 | Besson |
| 2008/0130979 A1 | 6/2008 | Ren et al. |
| 2008/0212861 A1 | 9/2008 | Durgan et al. |
| 2008/0285712 A1 | 11/2008 | Kopans |
| 2008/0317196 A1 | 12/2008 | Imai |
| 2009/0003519 A1 | 1/2009 | Defreitas et al. |
| 2009/0010384 A1 | 1/2009 | Jing et al. |
| 2009/0080594 A1 | 3/2009 | Brooks et al. |
| 2009/0080602 A1 | 3/2009 | Brooks et al. |
| 2009/0135997 A1 | 5/2009 | Defreitas et al. |
| 2009/0141859 A1 | 6/2009 | Gkanatsios et al. |
| 2009/0213987 A1 | 8/2009 | Stein et al. |
| 2009/0237924 A1 | 9/2009 | Ladewig |
| 2009/0238424 A1 | 9/2009 | Arakita et al. |
| 2009/0268865 A1 | 10/2009 | Ren et al. |
| 2009/0296882 A1 | 12/2009 | Gkanatsios et al. |
| 2009/0304147 A1 | 12/2009 | Jing et al. |
| 2010/0020937 A1 | 1/2010 | Hautmann |
| 2010/0020938 A1 | 1/2010 | Koch |
| 2010/0034450 A1 | 2/2010 | Mertelmeier |
| 2010/0054400 A1 | 3/2010 | Ren |
| 2010/0086188 A1 | 4/2010 | Ruth et al. |
| 2010/0091940 A1 | 4/2010 | Ludwig et al. |
| 2010/0150306 A1 | 6/2010 | Defreitas et al. |
| 2010/0189227 A1 | 7/2010 | Mannar |
| 2010/0195882 A1 | 8/2010 | Ren |
| 2010/0226475 A1 | 9/2010 | Smith |
| 2010/0290585 A1 | 11/2010 | Eliasson |
| 2010/0303202 A1 | 12/2010 | Ren |
| 2010/0313196 A1 | 12/2010 | De Atley et al. |
| 2011/0026667 A1 | 2/2011 | Poorter |
| 2011/0069809 A1 | 3/2011 | Defreitas et al. |
| 2011/0178389 A1 | 7/2011 | Kumar et al. |
| 2011/0188624 A1 | 8/2011 | Ren |
| 2011/0234630 A1 | 9/2011 | Batman et al. |
| 2011/0268246 A1 | 11/2011 | Dafni |
| 2012/0033868 A1 | 2/2012 | Ren |
| 2012/0051502 A1 | 3/2012 | Ohta et al. |
| 2012/0236987 A1 | 9/2012 | Ruimi |
| 2012/0238870 A1 | 9/2012 | Smith et al. |
| 2013/0028374 A1 | 1/2013 | Gkanatsios et al. |
| 2013/0211261 A1 | 8/2013 | Wang |
| 2013/0272494 A1 | 10/2013 | DeFreitas et al. |
| 2014/0044230 A1 | 2/2014 | Stein et al. |
| 2014/0044231 A1 | 2/2014 | Defreitas et al. |
| 2014/0086471 A1 | 3/2014 | Ruth et al. |
| 2014/0098935 A1 | 4/2014 | Defreitas et al. |
| 2014/0232752 A1 | 8/2014 | Ren et al. |
| 2014/0314198 A1 | 10/2014 | Ren et al. |
| 2014/0321607 A1 | 10/2014 | Smith |
| 2014/0376690 A1 | 12/2014 | Jing et al. |
| 2015/0049859 A1 | 2/2015 | DeFreitas et al. |
| 2015/0160848 A1 | 6/2015 | Gkanatsios et al. |
| 2015/0310611 A1 | 10/2015 | Gkanatsios et al. |
| 2016/0106383 A1 | 4/2016 | Ren et al. |
| 2016/0189376 A1* | 6/2016 | Bernard ............... G06T 11/006 382/132 |
| 2016/0209995 A1* | 7/2016 | Jeon ..................... G16H 40/63 |
| 2016/0220207 A1 | 8/2016 | Jouhikainen |
| 2016/0256125 A1 | 9/2016 | Smith |
| 2016/0270742 A9 | 9/2016 | Stein et al. |
| 2016/0302746 A1* | 10/2016 | Erhard ................. A61B 6/4452 |
| 2016/0331339 A1 | 11/2016 | Guo |
| 2017/0024113 A1 | 1/2017 | Gkanatsios et al. |
| 2017/0032546 A1* | 2/2017 | Westerhoff ........... G06T 7/0014 |
| 2017/0071562 A1* | 3/2017 | Suzuki .................. A61B 6/025 |
| 2017/0128028 A1 | 5/2017 | DeFreitas et al. |
| 2017/0135650 A1 | 5/2017 | Stein et al. |
| 2017/0316588 A1* | 11/2017 | Homann ............... G06T 11/008 |
| 2017/0319167 A1 | 11/2017 | Goto |
| 2018/0130201 A1 | 5/2018 | Bernard |
| 2018/0177476 A1 | 6/2018 | Jing et al. |
| 2018/0188937 A1 | 7/2018 | Gkanatsios et al. |
| 2018/0289347 A1 | 10/2018 | DeFreitas et al. |
| 2018/0344276 A1 | 12/2018 | DeFreitas et al. |
| 2019/0059830 A1 | 2/2019 | Williams |
| 2019/0095087 A1 | 3/2019 | Gkanatsios et al. |
| 2019/0200942 A1 | 7/2019 | DeFreitas |

(56) References Cited

U.S. PATENT DOCUMENTS

| | | | |
|---|---|---|---|
| 2019/0336794 | A1 | 11/2019 | Li |
| 2019/0388051 | A1* | 12/2019 | Morita .................. A61B 6/5264 |
| 2020/0029927 | A1 | 1/2020 | Wilson |

FOREIGN PATENT DOCUMENTS

| | | |
|---|---|---|
| DE | 102004051820 | 5/2006 |
| DE | 102010027871 | 10/2011 |
| EP | 0775467 | 5/1997 |
| EP | 0982001 | 3/2000 |
| EP | 1028451 | 8/2000 |
| EP | 1428473 | 6/2004 |
| EP | 1759637 | 3/2007 |
| EP | 1569556 | 4/2012 |
| EP | 2732764 | 5/2014 |
| EP | 2602743 | 11/2014 |
| EP | 2819145 | 12/2014 |
| EP | 3143935 | 3/2017 |
| JP | 53151381 U | 11/1978 |
| JP | 2001-346786 | 12/2001 |
| JP | 2002219124 | 8/2002 |
| JP | 2006-231054 | 9/2006 |
| JP | 2007-50264 | 3/2007 |
| JP | 2007-521911 | 8/2007 |
| JP | 2007229269 | 9/2007 |
| JP | 2008-67933 | 3/2008 |
| JP | 2008086471 | 4/2008 |
| JP | 2009500048 | 1/2009 |
| JP | 2012-509714 | 4/2012 |
| JP | 2012-511988 | 5/2012 |
| JP | 2015-530706 | 10/2015 |
| WO | WO 90/05485 | 5/1990 |
| WO | WO 9803115 | 1/1998 |
| WO | WO 98/16903 | 4/1998 |
| WO | WO 00/51484 | 9/2000 |
| WO | WO 03/020114 | 3/2003 |
| WO | WO 03037046 | 5/2003 |
| WO | WO 2003/057564 | 7/2003 |
| WO | WO 2004/043535 | 5/2004 |
| WO | WO 2005/051197 | 6/2005 |
| WO | WO 2005/110230 | 11/2005 |
| WO | WO 2005/112767 | 12/2005 |
| WO | WO 2006/055830 | 5/2006 |
| WO | WO 2006/058160 | 6/2006 |
| WO | WO 2007129244 | 11/2007 |
| WO | WO 2008072144 | 6/2008 |
| WO | WO 2009122328 | 10/2009 |
| WO | WO 2009136349 | 11/2009 |
| WO | WO 2010/070554 | 6/2010 |
| WO | WO 2013/184213 | 12/2013 |

OTHER PUBLICATIONS

Niklason et al., "Digital breast tomosynthesis: potentially a new method for breast cancer screening", In Digital Mammography, 1998, 6 pages.
Thurfjell, "Mammography screening: one versus two views and independent double reading", Acta Radiologica 35, No. 4, 1994, pp. 345-350.
"Essentials for life: Senographe Essential Full-Field Digital Mammography system", GE Health-care Brochure, MM-0132-05.06-EN-US, 2006, 12 pgs.
"Filtered Back Projection," (NYGREN) published May 8, 2007; URL:http://web.archive.org/web/19991010131715/http://www.owlnet.rice.edu/-.about.elec539/Projects97/cult/node2.html., 2 pgs.
"Lorad Selenia" Document B-BI-SEO US/Intl (May 2006) copyright Hologic 2006, 12 pgs.
ACRIN website, located at https://www.acrin.org/PATIENTS/ABOUTIMAGINGEXAMSANDAGENTS/ABOUTMAMMOGRAPHYANDTOMOSYNTHESIS.aspx, "About Mammography and Tomosynthesis", obtained online on Dec. 8, 2015, 5 pgs.
American College of Radiology website, located at http://www.acr.org/FAQs/DBT-FAQ, "Digital Breast Tomosynthesis FAQ for Insurers", obtained online on Dec. 8, 2015, 2 pages.
Aslund, Magnus, "Digital Mammography with a Photon Counting Detector in a Scanned Multislit Geometry", Doctoral Thesis, Dept of Physics, Royal Institute of Technology, Stockholm, Sweden, Apr. 2007, 51 pages.
Chan, Heang-Ping et al., "ROC study of the effect of stereoscopic imaging on assessment of breast lesions", Medical Physics, vol. 32, No. 4, Apr. 2005, 7 pgs.
Cole, Elodia, et al., "The Effects of Gray Scale Image Processing on Digital Mammography Interpretation Performance", Academic Radiology, vol. 12, No. 5, pp. 585-595, May 2005.
Digital Clinical Reports, Tomosynthesis, GE Brochure 98-5493, Nov. 1998, 8 pgs.
Dobbins, James T., "Digital x-ray tomosynthesis: current state of the art and clinical potential," Physics in Medicine and Biology, Taylor and Francis Ltd, London GB, vol. 48, No. 19, Oct. 7, 2003, 42 pages.
Federica Pediconi et al., "Color-coded automated signal intensity-curve for detection and characterization of breast lesions: Preliminary evaluation of a new software for Mr-based breast imaging", International Congress Series 1281 (2005) 1081-1086.
Grant, David G., "Tomosynthesis: a three-dimensional imaging technique", IEEE Trans. Biomed. Engineering, vol. BME-19, #1, Jan. 1972, pp. 20-28.
Japanese Office Action mailed in Application 2016-087710, dated Mar. 1, 2017, 5 pages.
Japanese Office Action mailed in Application 2017-001579, mailed Mar. 29, 2017, 1 page. (No English Translation.).
Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.
Mammographic Accreditation Phantom, http://www.cirsinc.com/pdfs/015cp.pdf. (2006), 2 pgs.
Niklason, Loren T. et al., "Digital Tomosynthesis in Breast Imaging", Radiology, Nov. 1997, vol. 205, No. 2, pp. 399-406.
Pisano, Etta D., "Digital Mammography", Radiology, vol. 234, No. 2, Feb. 2005, pp. 353-362.
Senographe 700 & 800T (GE); 2-page download on Jun. 22, 2006 from www.gehealthcare.com/inen/rad/whe/products/mswh800t.html.; Figures 1-7 on 4 sheets re lateral shift compression paddle, 2 pgs.
Smith, A., "Fundamentals of Breast Tomosynthesis", White Paper, Hologic Inc., WP-00007, Jun. 2008, 8 pgs.
Smith, Andrew, PhD, "Full Field Breast Tomosynthesis", Hologic White Paper, Oct. 2004, 6 pgs.
Wheeler F. W., et al. "Micro-Calcification Detection in Digital Tomosynthesis Mammography", Proceedings of SPIE, Conf-Physics of Semiconductor Devices, Dec. 11, 2001 to Dec. 15, 2001, Delhi, SPIE, US, vol. 6144, Feb. 13, 2006, 12 pgs.
Wu, Tao, et al. "Tomographic Mammography Using a Limited No. Of Low-Dose Cone-Beam Projection Images" Medical Physics, AIP, Melville, NY, vol. 30, No. 3, Mar. 1, 2003, p. 365-380.
Japanese Notice of Rejection in Application 2018-554775, dated Feb. 22, 2021, 10 pages.

* cited by examiner

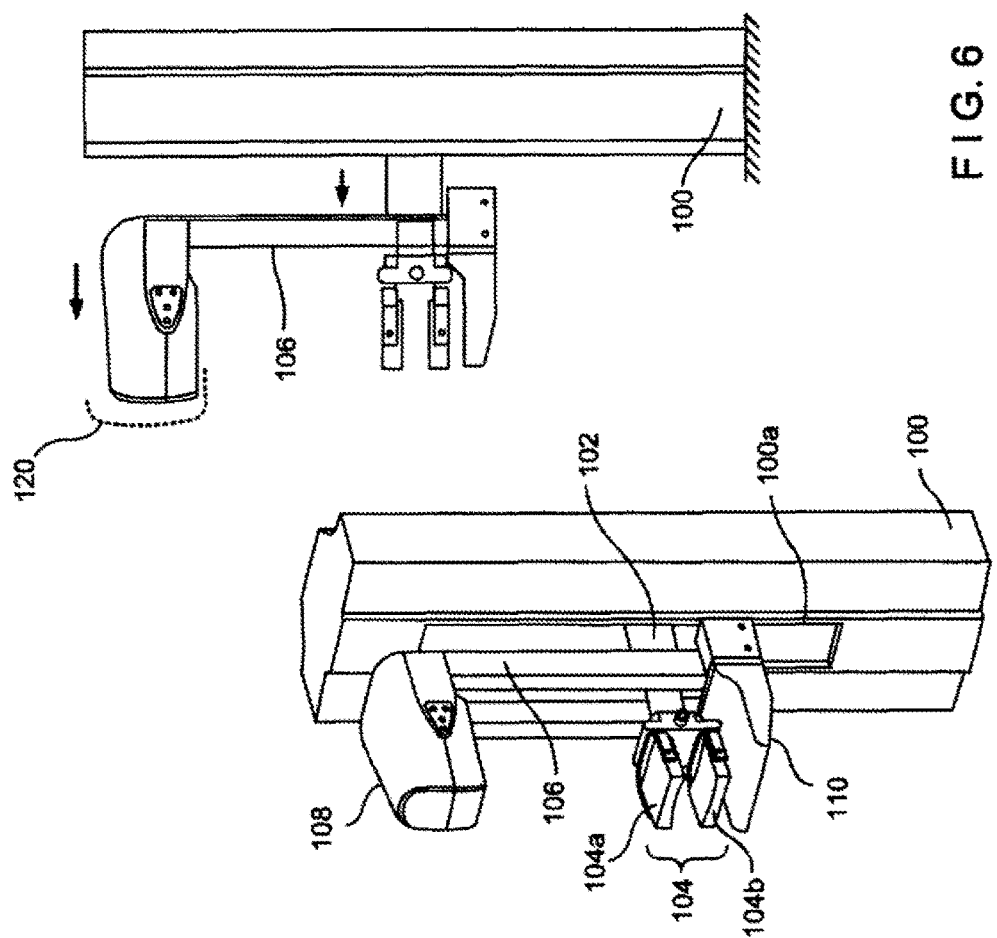

GENERATING SYNTHESIZED PROJECTION IMAGES FOR 3D BREAST TOMOSYNTHESIS OR MULTI-MODE X-RAY BREAST IMAGING

RELATED CASES

This application claims the benefit of U.S. Provisional Application No. 62/730,818 filed on Sep. 13, 2018, which is hereby incorporated by reference in its entirety.

BACKGROUND

Medical imaging has become a widely used tool for identifying and diagnosing abnormalities, such as cancers or other conditions, within the human body. Medical imaging processes such as mammography and tomography are particularly useful tools for imaging breasts to screen for, or diagnose, cancer or other lesions with the breasts. Tomosynthesis systems are mammography systems that allow high resolution breast imaging based on limited angle tomosynthesis. Tomosynthesis, generally, produces a plurality of x-ray images, each of discrete layers or slices of the breast, through the entire thickness thereof. In contrast to typical two-dimensional (2D) mammography systems, a tomosynthesis system acquires a series of x-ray projection images, each projection image obtained at a different angular displacement as the x-ray source moves along a path, such as a circular arc, over the breast. In contrast to conventional computed tomography (CT), tomosynthesis is typically based on projection images obtained at limited angular displacements of the x-ray source around the breast. Tomosynthesis reduces or eliminates the problems caused by tissue overlap and structure noise present in 2D mammography imaging. Acquiring each projection image, however, increases the total amount of time required to complete the imaging process.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for medical imaging through the use of a synthesized virtual projections generated from real projections. In an aspect, the technology relates to a system for generating images of a breast. The system includes an x-ray source, an x-ray detector, at least one processor operatively connected to the x-ray detector, and memory operatively connected to the at least one processor, the memory storing instructions that, when executed by the at least one processor, cause the system to perform a set of operations. The operations include, emitting, from the x-ray source, a first x-ray emission at a first angular location relative to the x-ray detector; detecting, by the x-ray detector, the first x-ray emission after passing through the breast; generating first x-ray imaging data from the detected first x-ray emission; emitting, from the x-ray source, a second x-ray emission at a second angular location relative to the breast; detecting, by the x-ray detector, the second x-ray emission after passing through the breast; generating second x-ray imaging data from the detected second x-ray emission; synthesizing, based on at least the first x-ray imaging data and the second x-ray imaging data, third x-ray imaging data for a third angular location relative to the breast, wherein the third angular location is different from the first angular location and the second angular location, thereby eliminating the need for an x-ray emission at the third angular location; and generating and displaying an image of the breast from the third x-ray imaging data.

In an example, the first x-ray imaging data is a first real projection for the first angular location, the second x-ray imaging data is a second real projection for the second angular location, and the third x-ray imaging data is a virtual projection for the third angular location. In another example, synthesizing the third x-ray imaging data includes fusing the first x-ray imaging data and the second x-ray imaging data in at least one of a spatial domain or a frequency domain. In yet another example, synthesizing the third x-ray imaging data further includes generating reconstruction data from the first x-ray imaging data and the second x-ray imaging data, and synthesizing the third x-ray imaging data is further based on the generated reconstruction data. In still another example, synthesizing the third x-ray imaging data further includes providing the first x-ray imaging data and the second x-ray imaging data into a trained deep-learning neural network and executing the trained deep-learning neural network based on the first x-ray imaging data and the second x-ray imaging data to generate the third x-ray imaging data. In still yet another example, the operations further comprise training a deep-learning neural network to generate the trained deep-learning neural network. Training the deep-learning neural network includes obtaining a set of real prior x-ray imaging data used for imaging a breast at multiple angular locations; dividing the set of real prior x-ray imaging data into a plurality of datasets comprising a training real data set for a first plurality of the angular locations and a training virtual data set for a second plurality of the angular locations, the second plurality of angular locations being different from the first plurality of angular locations; providing the training real data set as inputs into the deep-learning neural network; and providing the training virtual data set as a ground truth for the deep-learning neural network. In another example, the operations are performed as part of digital breast tomosynthesis or multi-modality imaging.

In another aspect, the technology relates to a computer-implemented method, executed by at least one processor, for generating images of a breast. The method includes receiving first real projection data for an x-ray emission from a first angular location relative to the breast; receiving second real projection data for an x-ray emission emitted from a second angular location relative to the breast; receiving third real projection data for an x-ray emission from a third angular location relative to the breast; and executing a synthesization process. The synthesization process is executed to generate, based on the first real projection data and the second real projection data, first virtual projection data for an x-ray emission from a fourth angular location relative to the breast, wherein the fourth angular location is different from the first angular location and the third angular location; and generate, based on the second real projection data and the third real projection data, second virtual projection data for an x-ray emission from a fifth angular location relative to the breast, wherein the fifth angular location different from the second angular location and the fourth angular location. The method further includes determining that at least one of the first virtual projection data or the second virtual projection data has a quality outside of a predetermined tolerance; based on the determination that the at least one of the first virtual projection or the second virtual projection has a quality outside of a predetermined tolerance, modifying the synthesization process to create a modified synthesization process; executing the modified synthesization process to generate a modified first virtual projection and a modified second virtual projection; generating a reconstruction model from the first real projection data, the second real projection data, the third real projection data, the modified first virtual projection data, and the modified second virtual projection data; and displaying at least one of a slice of the breast from the generated reconstruction model, the first real projection data, the second real projection data, the third real projection data, the first virtual projection data, or the second virtual projection data.

In an example, determining that at least one of the first virtual projection data or the second virtual projection data has a quality outside of a predetermined tolerance further includes: identifying a landmark in one of the first real projection data or the second real projection data; identifying the landmark in the first virtual projection data; comparing the location of the landmark in the first virtual projection data to the location of the landmark in at least one of the first real projection data or the second real projection data; and based on the comparison, determining whether the location of the landmark in the first virtual projection data is within the predetermined tolerance. In another example, the synthesization process includes: providing the first real projection data, the second real projection data, the third real projection data into a trained deep-learning neural network; and executing the trained deep-learning neural network based on the first real projection data, the second real projection data, the third real projection data to generate the first virtual projection data and the second virtual projection data. In yet another example, modifying the synthesization process includes modifying coefficients of the trained deep-learning neural network. In still another example, the method further includes determining that the slice has a quality outside a reconstruction quality tolerance; and based on the determination that the slice has a quality outside a reconstruction quality tolerance, further modifying the modified synthesization process to create a further modified synthesization process. In still yet another example, the method further includes: executing the further modified synthesization process to generate a further modified first virtual projection data and a further modified second virtual projection data; generating a modified reconstruction model from the first real projection data, the second real projection data, the third real projection data, the further modified first virtual projection data, and the further modified second virtual projection data; and displaying at least one of a slice of the breast from the modified reconstruction model, the further modified first virtual projection, or the further modified second virtual projection. In another example, the method is performed as part of digital breast tomosynthesis or multi-modality imaging.

In another aspect, the technology relates to another computer-implemented method, executed by at least one processor, for generating images of a breast. The method includes receiving first real projection data for an x-ray emission from a first angular location relative to the breast; receiving second real projection data for an x-ray emission emitted from a second angular location relative to the breast; providing the first real projection data and the second real projection data into a trained deep-learning neural network; executing the trained deep-learning neural network based on the first real projection data, and the second real projection data to generate first virtual projection data for a third angular location relative to the breast; generating a reconstruction model from the first real projection data, the second real projection data, and the first virtual projection data; and displaying at least one of a slice of the breast from the generated reconstruction model, the first real projection data, the second real projection data, or the first virtual projection data.

In an example, the method further includes determining that the slice has a quality outside a reconstruction quality tolerance; and based on the determination that the slice has a quality outside a reconstruction quality tolerance, modifying the trained deep-learning neural network to create a modified deep-learning neural network. In another example, the method further includes: executing the modified deep-learning neural network based on the first real projection data and the second real projection data to generate a modified first virtual projection; generating a modified reconstruction model from the first real projection data, the second real projection data, and the modified first virtual projection data; and displaying at least one of a slice of the breast from the modified reconstruction model or the modified first virtual projection. In yet another example, the determination that the slice has a quality outside a reconstruction quality tolerance is based on at least one of image artifacts or image quality measurements. In still another example, the difference between the first angular location and the second angular location is less than or equal to three degrees. In still yet another example, the method is performed as part of digital breast tomosynthesis or multi-modality imaging.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

FIGS. 5 and 6 are similar to FIGS. 1 and 2, respectively, but illustrate the system as used in a tomosynthesis mode or a mammography mode and shows a gantry that is spaced further from a support column than in FIGS. 2 and 4.

DETAILED DESCRIPTION

Figure 2:
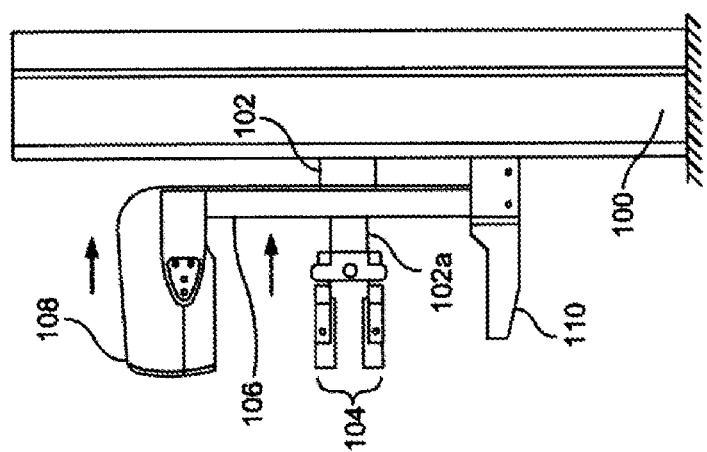
FIG. 2 is a side elevation of the system of FIG. 1.

As discussed above, a tomosynthesis system acquires a series of x-ray projection images, each projection image obtained at a different angular displacement as the x-ray source moves along a path, such as a circular arc, over the breast. More specifically, the technology typically involves taking two-dimensional (2D) real projection images of the immobilized breast at each of a number of angles of the x-ray beam relative to the breast. The resulting x-ray measurements are computer-processed to reconstruct images of breast slices that typically are in planes transverse to the x-ray beam axis, such as parallel to the image plane of a mammogram of the same breast, but can be at any other orientation and can represent breast slices of selected thicknesses. Acquiring each real projection image introduces additional radiation to the patient and increases the total amount of time required to complete the imaging process. The use of fewer real projection images, however, leads to worse image quality for the reconstructed images.

The present technology contemplates systems and methods that allow fewer real projection images to be acquired, while still preserving suitable image quality of reconstructed images of breast slices. The present technology allows for virtual projection images to be generated from real projection images. The virtual projection images may then be used, along with the real projection images, to generate the reconstruction model for the breast. Through the use of the virtual projection images, radiation exposure at some of the angular locations where radiation exposure was traditionally necessary can be eliminated—thus reducing the total radiation dose received by the patient and reducing the time required to complete the tomosynthesis procedure. Reducing the amount of time the patient is imaged also improves image quality by reducing the amount of movement or motion of the patient during the imaging procedure.

In some examples the total imaging time and dosage may remain the same as prior imaging procedures, such as tomosynthesis imaging procedures. In such examples, the virtual projection images may be generated to expand the angular range that is images or provide additional information for the real projection images. Thus, imaging artifacts in the reconstruction images, such as overlay structures or other imaging artifacts that are inherent in limited-angle imaging modalities, may be reduced or removed due to the additional virtual projections.

The virtual projection images may be generated from machine-learning techniques, such a deep-learning neural networks. The virtual projection images may also be generated by fusing multiple real projection images. In addition, generating the virtual projection images may be based on reconstruction data generated from the real projection images. The generation of the virtual projections and reconstruction data may also be an iterative process. For example, image quality of a reconstructed breast slice may be assessed, and if the quality is poor, modified virtual projections can be generated to improve the image quality of the image of the breast slice until a desired performance criteria is achieved. As used herein, a real projection refers to a projection obtained by emitting radiation through the breast for a respective angular location. In contrast, a virtual projection refers to a projection obtained without emitting radiation through the breast.

In describing examples and embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Figure 1:
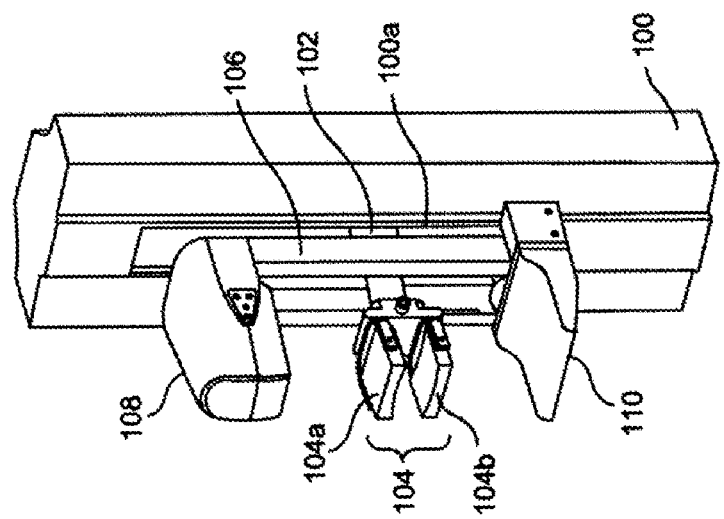
FIG. 1 depicts a perspective view of a portion of an upright breast x-ray imaging system.
Figure 4:
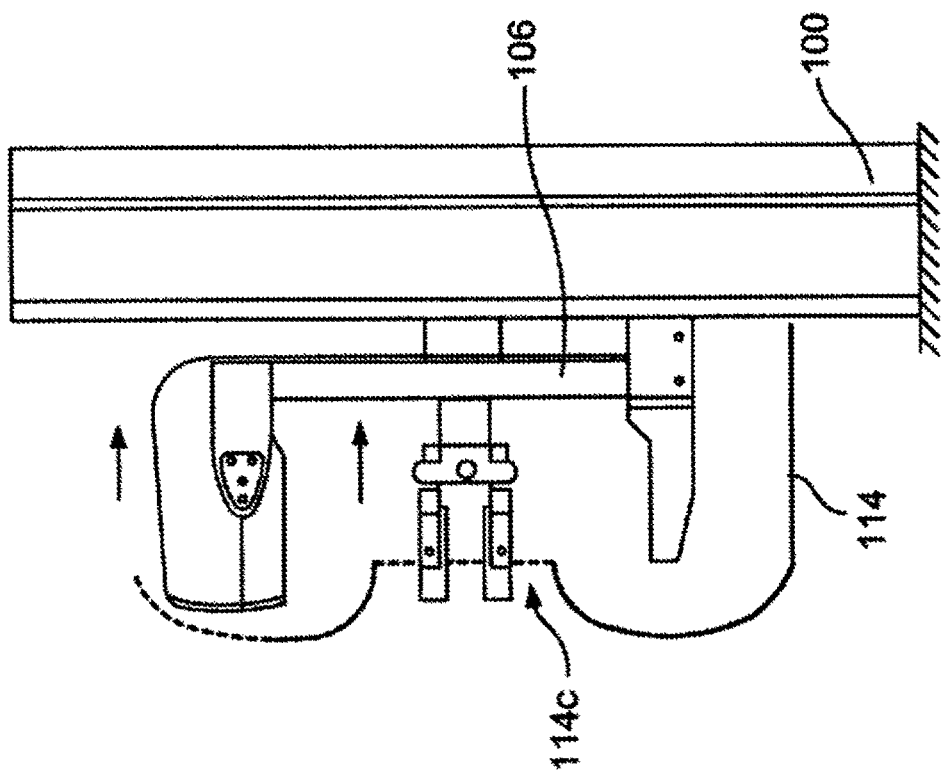
FIG. 4 is a side elevation that is the same as FIG. 2 but illustrates a patient shield.
Figure 3:
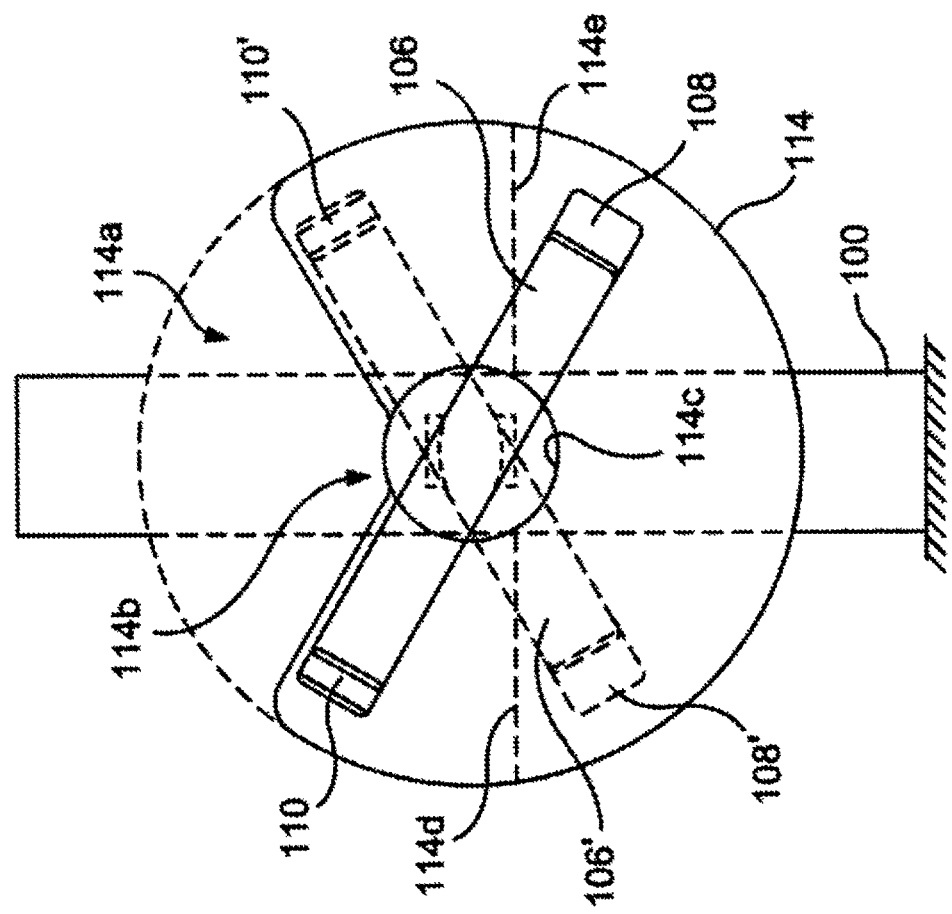
FIG. 3 is a front elevation illustrating a patient shield for a system similar to that seen in FIGS. 1 and 2.

FIGS. 1 and 2 illustrate portions of a non-limiting example of a multi-mode breast x-ray imaging system operable in a CT mode but also configured to selectively operate in a tomosynthesis mode including a wide angle tomosynthesis mode and a narrow angle tomosynthesis mode, and in a mammography mode. For clarity of illustration, a patient shield for use in the CT mode is omitted from FIGS. 1 and 2 but examples are illustrated in FIGS. 3 and 4. A support column 100 is secured to a floor and houses a motorized mechanism for raising and lowering a horizontally extending axle 102, which protrudes through an opening 100a in column 100, and for rotating axle 102 about its central axis. Axle 102 in turn supports a coaxial axle 102a that can rotate with or independently of axle 102. Axle 102 supports a breast immobilization unit comprising an upper plate 104a and a lower plate 104b such that each plate can move up and down along the long dimension of support 100 together with axles 102 and 102a, at least one of the plates can move toward the other, and unit 104 can rotate about the common central axis of axles 102 and 102a. In addition, axle 102 supports a gantry 106 for two types of motorized movement: rotation about the central axis of axle 102, and motion relative to axle 102 along the length of gantry 106. Gantry 106 carries at one end an x-ray source such as a shrouded x-ray tube generally indicated at 108, and at the other end a receptor housing 110 enclosing an imaging x-ray detector or receptor 112.

When operating in a CT mode, the system of FIGS. 1 and 2 immobilizes a patient's breast between plates 104a and 104b. To this end, unit 104 is raised or lowered together with axle 102 to the height of the breast while the patient is upright, e.g., standing or sitting. The patient leans toward unit 104 from the left side of the system as seen in FIG. 2, and a health professional, typically an x-ray technician, adjusts the breast between plates 104a and 104b while pulling tissue to the right in FIG. 2 and moving at least one of plates 104a and 104b toward the other to immobilize the breast and keep it in place, preferably with as much as practicable of the breast tissue being inside unit 104. In the course of taking x-ray measurements representing real projection x-ray images, from which to reconstruct images of respective breast slices, gantry 106 rotates about the central axis of axle 102 while the breast remains immobilized in unit 104. Imaging receptor 112 inside housing 110 remains fixed relative to x-ray tube 108 during the rotation of gantry 106. A pyramid shaped beam of x-rays from tube 108 traverses the breast immobilized in unit 104 and impinges on imaging receptor 112, which in response generates a respective two-dimensional array of pixel values related to the amount of x-ray energy received for each increment of rotation at respective pixel positions in an imaging plane of the receptor. These arrays of pixel values for real projection images are delivered to and processed by a computer system to reconstruct slice images of the breast. Gantry 106 may be configured for motorized movement toward column 100, to facilitate the x-ray technician's access to the patient's breast for positioning the breast in unit 104, and away from column 100 to ensure that x-ray tube 108 and imaging receptor 112 inside housing 110 can image the appropriate breast tissue. Alternatively, gantry 106 can maintain a fixed distance from column 100, to the left of the position seen in FIG. 2, so that the imaging x-ray beam can pass through as much as practical of the breast immobilized in unit 104, in which case there would be no need for a mechanism to vary that distance.

A unique challenge arises because of the upright position of the patient and the rotation of x-ray tube 108 and receptor housing 110 through a large angle in the CT mode of operation. As known, CT scanning typically involves a rotation of the source and receptor through an angle of 180° plus the angle subtended by the imaging x-ray beam, and preferably a rotation through a greater angle, e.g., 360°. However, if the rotation includes the 0° position of x-ray source 108 as seen in FIGS. 1 and 2, the patient's head may be too close to x-ray source 108. Collision of rotating assemblies with the patient, and concern with such collision, can be avoided by the use of a shield separating the patient from assemblies rotating even the full 360, as discussed below in this patent specification, although depending on the design of the shield and the rotating assemblies in particular embodiments this may require the patient to arch her body such that both her head and legs are away from the system, to the left as seen in FIG. 2. An alternative, also discussed below, is to exclude from the rotation a sector or segment around the position of x-ray source 108 seen in FIGS. 1 and 2. As a non-limiting example, if the position of x-ray tube 108 seen in FIGS. 1 and 2 is designated the 0° position, then the rotation for CT imaging excludes positions of x-ray source 108 in the 90° sector or segment between 45° and 315°, or in the 120° sector or segment between 60° and 300°, or in some other sector or segment that is sufficient to clear the patient's head position while taking x-ray CT data over a sufficient angle of rotation for the reconstruction of high quality slice images. While the rotation of x-ray tube 108 and receptor housing 110 still has to clear the lower part of the patient's body, it is generally easier for a patient to keep the lower part of her body away from the rotating components, to the left as seen in FIG. 2 (and preferably behind a shield), than to arch back her head and shoulders.

An example of such a shield is illustrated in FIGS. 3 and 4. FIG. 4 is a side elevation that is otherwise the same as FIG. 2 but additionally illustrates a patient shield 114 having a central opening 114c. Shield 114 may be completely circular in front elevation, as illustrated by the circle that includes an arc in broken line in FIG. 3, in front elevation. In that case, gantry 106 can rotate through a complete circle in the CT mode. As an alternative, shield 114 can leave open a sector or segment 114a illustrated in FIG. 3 as the area below the broken line arc and between the solids line of shield 114. In that case, gantry 106 can rotate in the CT mode only through an angle that is less than 360°, but the patient can have space for her head and perhaps a shoulder and an arm in the V-shaped cutout 114b of shield 114, for a more comfortable body posture. Specifically, as illustrated in FIG. 3, gantry 106 can rotate only within the portion of shield 114 that is outside V-shaped cutout 114b. One of the possible positions of gantry 106 and tube 108 and receptor housing 110 is shown in solid lines. Another possible position is shown in broken lines, and designated as gantry 106', carrying x-ray source 108' and receptor housing 110'. FIG. 4 illustrates a possible shape of shield 114 in side elevation.

Use of the system in a tomosynthesis mode is illustrated in FIGS. 5 and 6, which are otherwise the same as FIGS. 1 and 2 respectively, except that gantry 106 is in a different position relative to breast immobilization unit 104 and axle 102 and column 100, and no shield 114 is shown. In particular, x-ray source 108 is further from unit 104 and column 100, and receptor housing 110 is closer to unit 104. In the tomosynthesis mode, the patient's breast also is immobilized between plates 104a and 104b, which remain in place during imaging. In one example, x-ray tube 108 and receptor housing 110 may undergo a rotation about the immobilized breast that is similar to that in the CT mode operation but is through a smaller angle. A respective two-dimensional projection image Tp taken for each increment of rotation while x-ray tube 108 and imaging receptor 112 inside housing 110 rotate as a unit, fixed with respect to each other, as in the CT mode or as illustrated in principle in commonly assigned U.S. Pat. No. 7,123,684, the disclosure of which is hereby incorporated by reference herein in its entirety. Alternatively, the motions of x-ray tube 108 and receptor 112 relative to the immobilized breast can be as in said system offered under the trade name Selenia® Dimensions® of the common assignee, certain aspect of which are described in commonly owned U.S. Pat. No. 7,616,801, the disclosure of which is hereby incorporated by reference herein in its entirety. In this alternative case, x-ray tube rotates about the central axis of axle 102, but receptor housing 110 remains in place while imaging receptor 112 rotates or pivots inside housing 110 about an axis that typically passes through the image plane of the receptor, is parallel to the central axis of axle 102, and bisects imaging receptor 112. The rotation or pivoting of receptor 112 typically is through a smaller angle than the rotation angle of x-ray tube 108, calculated so that a normal to the imaging plane of receptor 112 can continue pointing at or close to the focal spot in x-ray tube 108 from which the imaging x-ray beam is emitted, and so that the beam continues to illuminate all or most of the imaging surface of receptor 112.

In one example of tomosynthesis mode operation, x-ray tube 108 rotates through an arc of about ±15° while imaging receptor rotates or pivots through about ±5° about the horizontal axis that bisects its imaging surface. During this motion, plural projection images RP are taken, such as 20 or 21 images, at regular increments of rotation angle. The central angle of the ±15° arc of x-ray source 108 rotation can be the 0° angle, i.e., the position of the x-ray source 108 seen in FIGS. 5 and 6, or some other angle, e.g., the angle for the x-ray source position typical for MLO imaging in conventional mammography. In the tomosynthesis mode, the breast may be immobilized in unit 104 but, alternatively, lower plate 104b may be removed so that the breast is supported between the upper surface of receptor housing 110 and upper plate 104a, in a manner analogous to the way the breast is immobilized in said system offered under the trade name Selenia®. In the tomosynthesis mode, greater degree of breast compression can be used under operator control than in the CT mode. The same concave plates 104a and 104b can be used, or generally flat plates can be substituted, or a single compression paddle can be used while the breast is supported by the upper surface of receptor housing 110, as used in said system offered under the Selenia® trade name.

When operating in a tomosynthesis mode, the system of FIGS. 5 and 6 provides multiple choices of that mode, selectable by an operator, for example a narrow angle mode and a wide angle mode. In the narrow angle tomosynthesis mode, x-ray source 108 rotates around unit 104 and the patient's breast immobilized therein through an angle such as ±15°, while in the wide angle tomosynthesis mode x-ray tube 108 rotates through an angle such as in the range of about ±15° to ±60°. The wide angle mode may involve taking the same number of projection images RP as the narrow angle mode, or a greater number. As a non-limiting example, if the narrow angle mode involves taking a total or 20 or 21 tomosynthesis projection images RP as x-ray source 108 moves through its arc around the breast, the wide angle mode may involve taking the same number of images RP or a greater number, such as 40 or 60 or some other number, typically at regular angular increments. The examples of angles of rotation of x-ray source 108 are not limiting. The important point is to provide multiple modes of tomosynthesis operations, where one mode involves x-ray source rotation through a greater angle around the breast than another tomosynthesis mode. Additional details regarding the structure and operation of image system of FIGS. 1-6 are provided in U.S. Pat. No. 8,787,522, the disclosure of which is hereby incorporated by reference herein in its entirety. The methods and systems described herein may be implemented in digital breast tomosynthesis (DBT) procedures as well as multi-modality imaging (MMI) procedures. MMI procedures generally refers to the use of a combination of different imaging modes or techniques, such as DBT acquisitions with varying dosage levels and/or angular coverage, computerized tomography (CT) of a compressed breast, and/or a combination of the two.

Figure 7A:
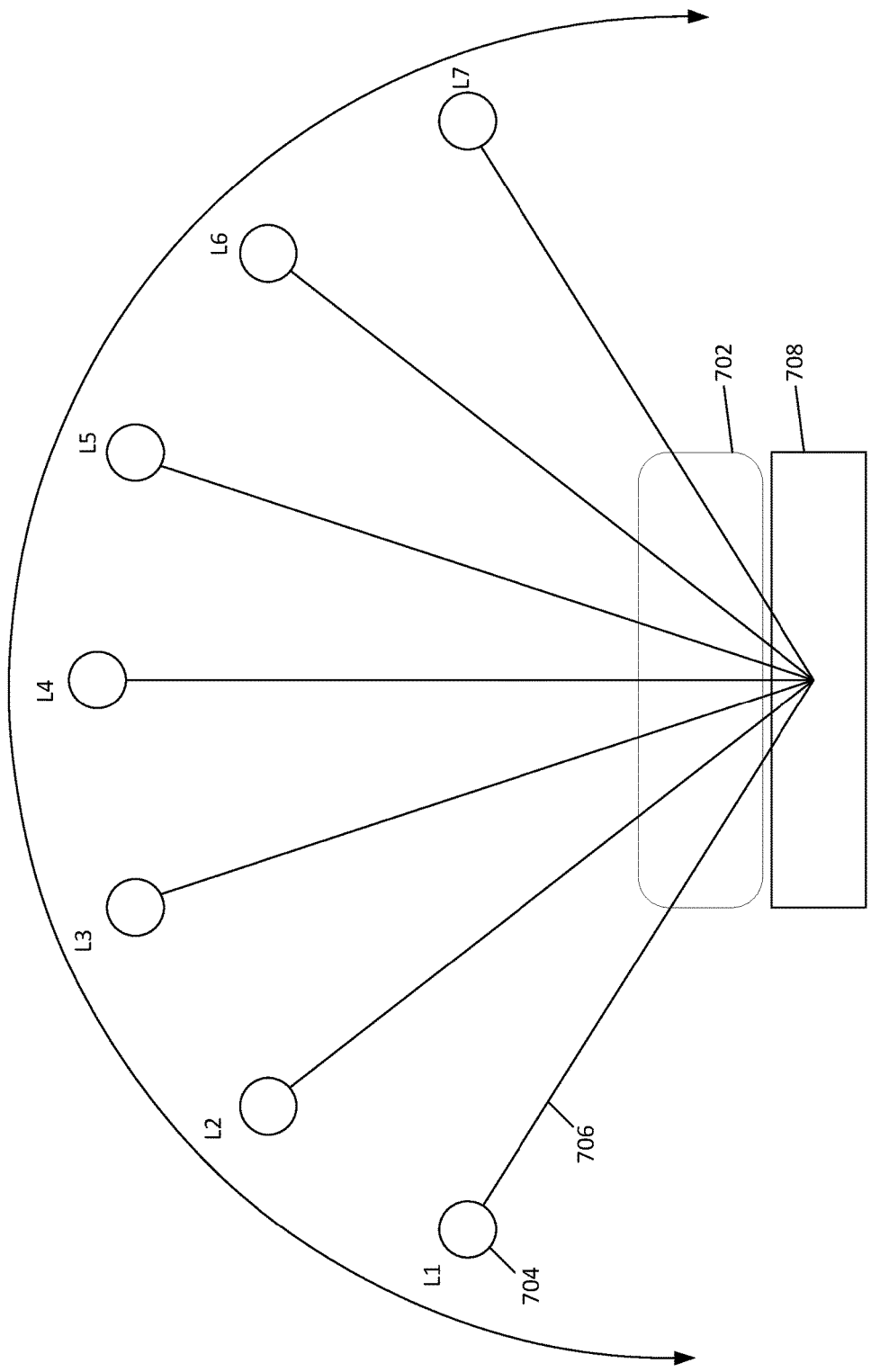
FIG. 7A depicts an example of plurality of angular locations relative to a compressed breast for real projections.

FIG. 7A depicts an example of plurality of angular locations (L1-L7) relative to a compressed breast 702 for real projections. At each of the plurality of angular locations (L1-L7) a real projection image may be acquired. For example, at angular location L1, an x-ray source 704 emits an x-ray emission 706 that passes through the compressed breast and is then detected by an x-ray receptor or detector 708, which allows for processing of the detected x-ray emission to form a real projection image for angular location L1. Subsequently, the x-ray source 704 moves to angular location L2, where an x-ray emission 706 is emitted that passes through the compressed breast and is then detected by the x-ray detector 708, which allows for processing of the detected x-ray emission to form a real projection image for angular location L2. This process continues for each of the angular locations L1-L7. While there are only seven angular locations depicted in the figure, such a depiction is for illustrative purposes. In implementation, more or fewer angular locations may be used. In addition, the positions of the angular locations may also differ in different examples. In some examples, the difference between each angular location may be less than or equal to three degrees. In other examples, the difference between each angular location may be less than or equal to one degree.

Figure 7B:
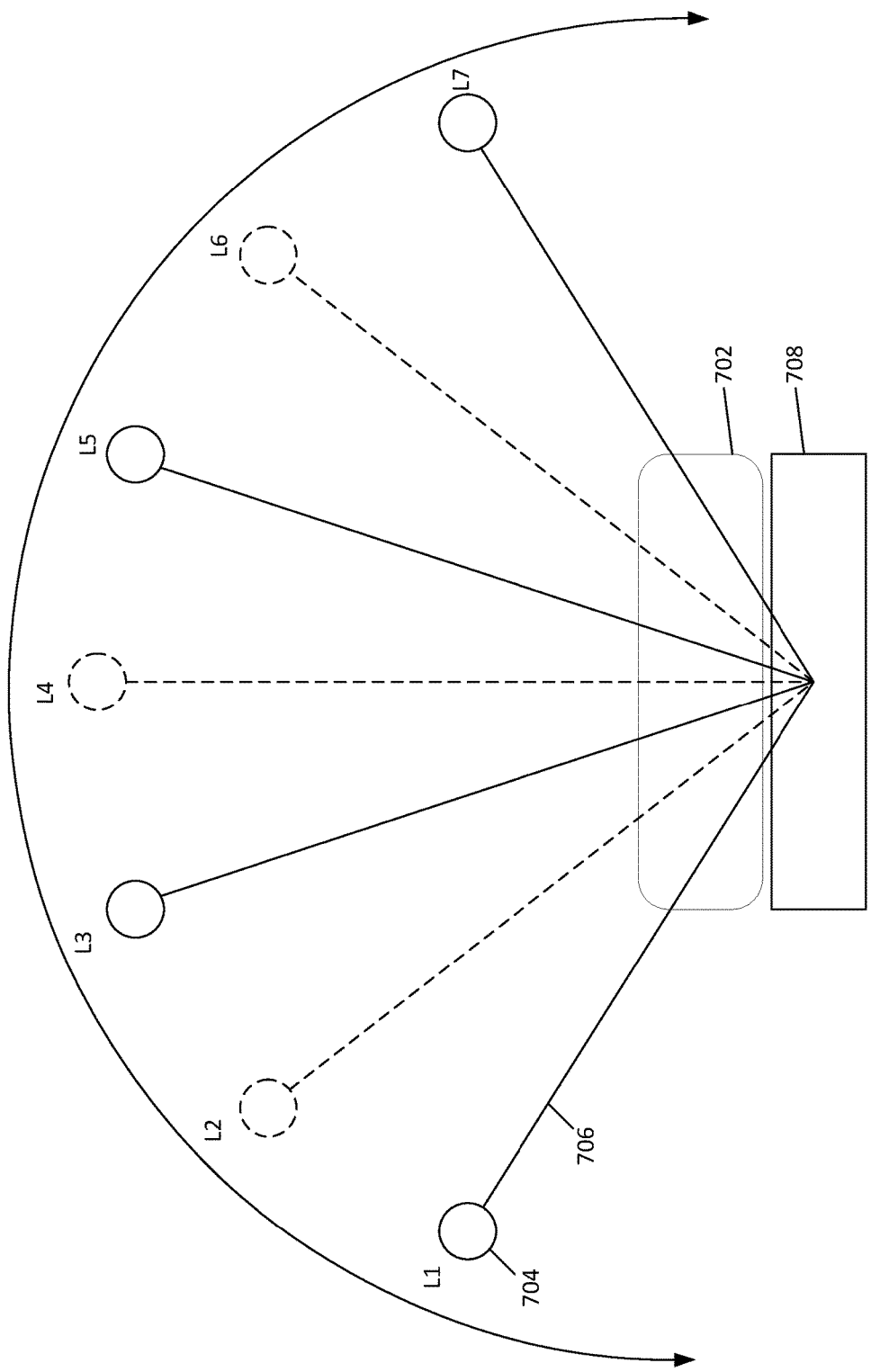
FIG. 7B depicts an example of plurality of angular locations relative to a compressed breast for real projections and virtual projections.

FIG. 7B depicts an example of plurality of angular locations (L1-L7) relative to a compressed breast 702 for real projection and virtual projections. In FIG. 7B, the angular locations for real projections are indicated by solid lines and the angular locations for virtual projections are indicated by dashed lines. More specifically, in the example depicted, real projections are acquired at angular locations L1, L3, L5, and L7. Virtual projections are then generated for angular locations L2, L4, and L6. The virtual projections may be synthesized, or otherwise generated, based on the acquired virtual projections. For example, the virtual projection for angular location L2 may be generated based on the real projections acquired for angular locations L1 and L3. The virtual projection for angular location L2 may be based on other acquired angular locations as well.

Figure 7C:
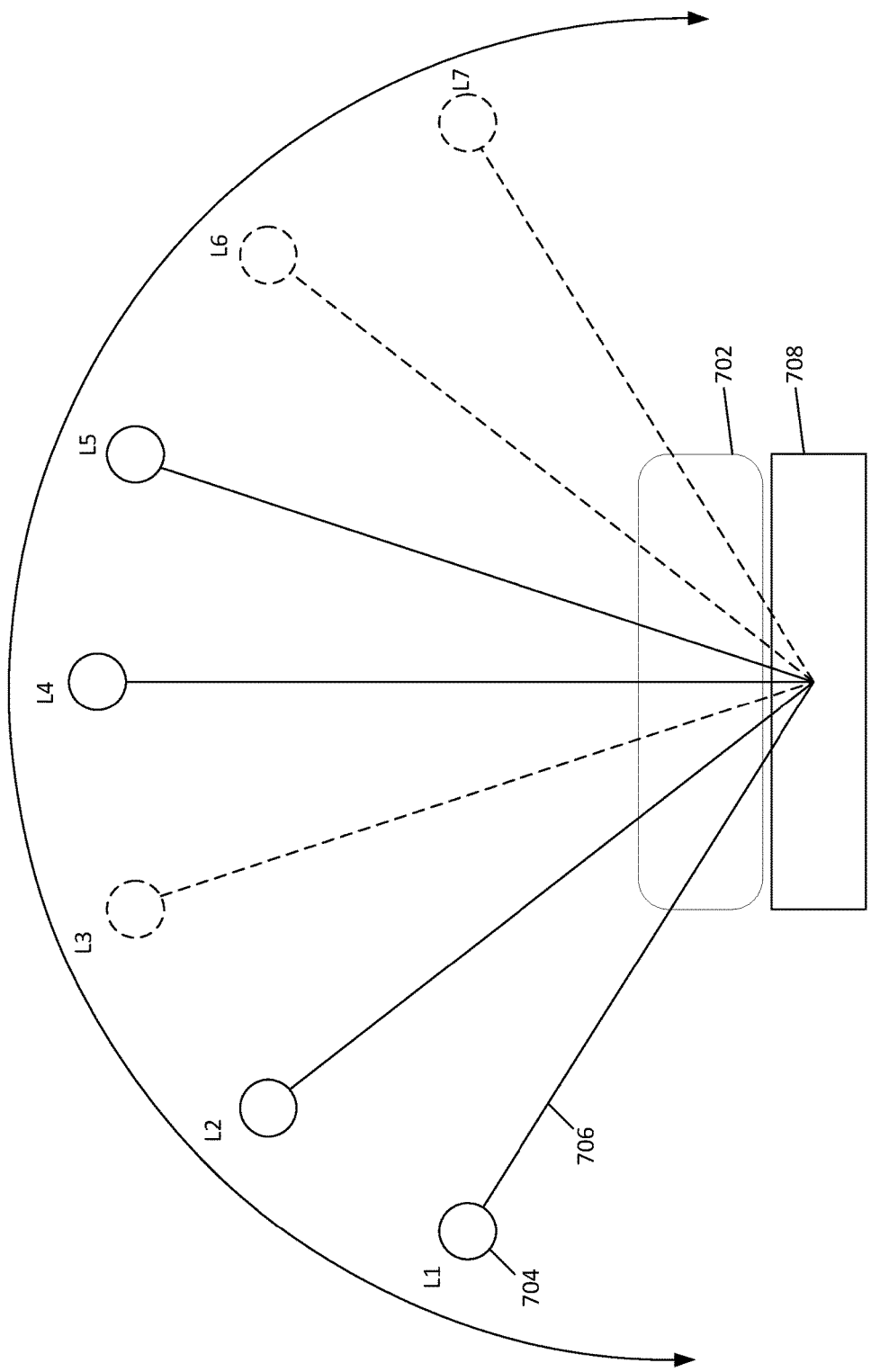
FIG. 7C depicts an example of plurality of angular locations relative to a compressed breast for real projections and virtual projections.

In other examples, angular locations for real projections and virtual projections need not alternate as shown in FIG. 7B. As an example, FIG. 7C depicts an example of plurality of angular locations (L1-L7) relative to a compressed breast 702 for real projection and virtual projections. In the example depicted in FIG. 7C, real projections are acquired at angular locations L1, L2, L4, and L5. Virtual projections are generated for angular locations L3, L6, and L7. Each of the virtual projections may be generated based on any combination of the acquired real projections. For instance, the virtual projection for angular location L7 may be generated based on the acquired real projections for angular locations L1, L2, L4, and L5. While a few different examples of angular locations for real and virtual projections have been provided herein, the technology is not limited to such combinations. Other combinations of angular locations for real and virtual projections are also contemplated.

Figure 8B:
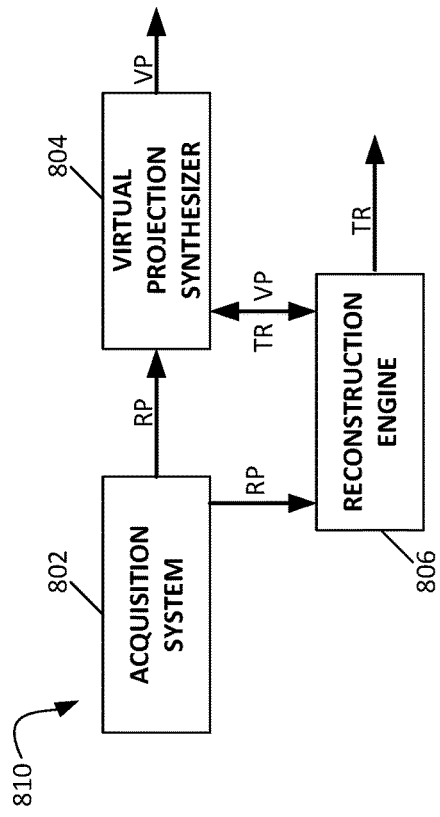
FIG. 8B depicts another example system for synthesizing virtual projections.
Figure 8C:
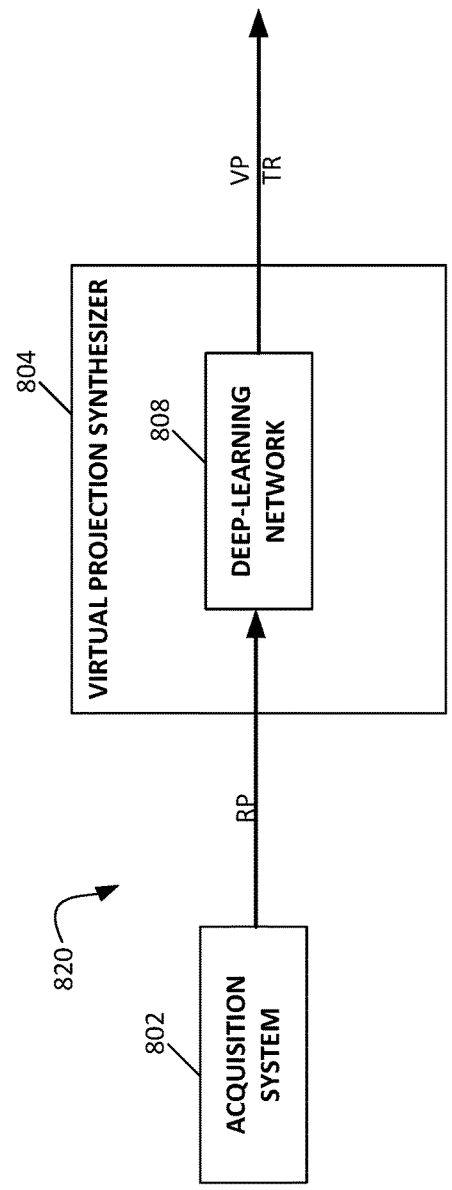
FIG. 8C depicts another example system for synthesizing virtual projections.
Figure 8A:
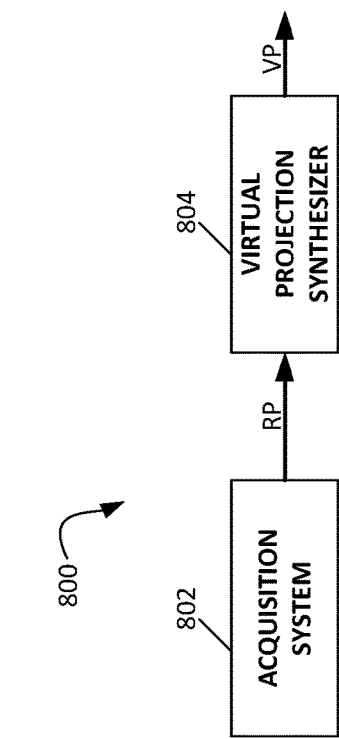
FIG. 8A depicts an example system for synthesizing virtual projections.

FIG. 8A depicts an example system 800 for synthesizing virtual projections (VP). The system 800 includes an acquisition system 802 and a virtual projection synthesizer 804. The acquisition system may include one or more of the imaging system(s) discussed above in FIGS. 1-6, which are capable of acquiring real projections (RP). The real projections (RP) are provided to a virtual projection synthesizer 804. The virtual projection synthesizer 804 synthesizes virtual projections (VP) based on the real projections (RP) received from the acquisition system 802. The virtual projection synthesizer 804 may be part of a computing system attached to the acquisition system 802, such as a workstation, or another computing system operatively connected to the acquisition system 802 such that the virtual projection synthesizer 804 may receive the real projections (RP). The virtual projection synthesizer 804 may fuse at least a portion of the real projections (RP) to synthesize the virtual projections (VP). The virtual projections (VP) and the real projections (RP) may then be used together to generate a reconstruction model.

Fusing the real projections (RP) to synthesize or generate virtual projections (VP) may be performed by a variety of image analysis and combination techniques, including superposition, interpolation, and extrapolation techniques, among other potential techniques. Interpolation or extrapolation techniques may be performed based on the angular locations of the real projections (RP) as compared to the corresponding angular location of the virtual projection (VP). For instance, where the angular location of the virtual projection (VP) is between the angular locations of the real projections (RP) used to generate the virtual projection (VP), interpolation techniques may be used. Where the angular location of the virtual projection (VP) is outside the angular locations of the real projections (RP) used to generate the virtual projection (VP), extrapolation techniques may be used. The techniques for fusing the real projections (RP) to generate virtual projections (VP) may also be performed in the spatial, transform, or frequency domains. For example, image fusion techniques in the spatial domain generally operate based on the pixel values in the real projections (RP). Image fusion techniques within the transform or frequency domains generally operate based on mathematical transforms, such as a Fourier or Laplace transform, of the pixel data from the real projections (RP). For instance, in the frequency domain, the image fusion techniques may be based on a rate of change of pixel values within the spatial domain.

FIG. 8B depicts another example system 810 for synthesizing virtual projections. Similar to the system 800, the system 810 includes the acquisition system 802 and the virtual projection synthesizer 804. The system 810 also includes a reconstruction engine 806. The reconstruction engine 806 generates a reconstruction model and reconstruction images TR, such as images for slices of breasts as discussed above. The reconstruction engine 806 receives the real projections (RP) from the acquisition system 802 and receives the virtual projections from the virtual projection synthesizer 804. The reconstruction engine 806 then generates the reconstruction model and reconstruction images (TR) based on the received real projections (RP) and the received virtual projections (VP).

In the system 810, the virtual projection synthesizer 804 may also use reconstruction images (TR) to generate the virtual projections (VP). In one example, the virtual projection synthesizer 804 receives reconstruction images (TR) from the reconstruction engine 806. In such an example, the reconstruction images (TR) may be based on the real projections (RP) received by the reconstruction engine 806 from the acquisition system 802. In other examples, the process of generating the reconstruction images (TR) and/or the virtual projections (VP) may be an iterative process. For instance, the reconstruction engine 806 may receive the real projections (RP) from the acquisition system 802 and the virtual projections (VP) from the virtual projection synthesizer 804 generated from the real projections (RP). The reconstruction engine 806 then generates the reconstruction images (TR) from the real projections (RP) and the virtual projections (VP). Those reconstruction images (TR) may be provided back to the virtual projection synthesizer 804 to update the virtual projections (VP) based on the reconstruction images (TR). The updated or modified virtual projections (VP) may then be provided back to the reconstruction engine 806 to generate an updated or modified reconstruction model and updated reconstruction images (TR). This iterative updating or modification process may continue until performance criteria for the virtual projection or a performance criteria for the reconstruction images, or both, is achieved.

FIG. 8C depicts another example system 820 for synthesizing virtual projections (VP). The system 820 is similar to the system 800 depicted in FIG. 8A, with the exception that the virtual projection synthesizer 804 includes at least one deep-learning neural network 808. The deep-learning neural network 808 receives at least a portion of the real projections (RP) from the acquisition system 802. The deep-learning neural network 808 processes the received real projections (RP) to synthesize or generate the virtual projections (VP).

Prior to receiving the real projections (RP), the deep-learning neural network 808 has been trained to generate the virtual projections (VP). For instance, the deep-learning neural network 808 may be trained with a known set of real projection data. The real projection data may be separated into a set of training real projection data and training virtual projection data. As an example, real projection data may be received for angular locations L1, L2, and L3. The real projection data for angular location L2 may be segregated into a data set of training virtual projection data. The real projection data for angular location L2 is effectively the desired, or ideal, virtual projection data for angular location L2. As such, the deep-learning neural network 808 can be trained to produce virtual projection data based on former real projection data. The real projection data for angular locations L1 and L3 is used as input during training, and the known virtual projection data for the angular location L2 is used as a ground truth during training. Training the deep-learning neural network 808 may be performed using multiple different techniques. As one example, the coefficients of the deep-learning neural network 808 may be adjusted to minimize a pre-defined cost function that evaluates the difference between the known virtual projection data and the output of the deep-learning neural network 808 during training. Multiple sets of real projection data may be used to train the deep-learning neural network 808 until a desired performance of the deep-learning neural network 808 is achieved.

In other examples, the deep-learning neural network 808 may be used to generate a reconstruction model or reconstruction images (TR) without an intermediate operation of generating virtual projections (VP). In such an example, the deep-learning neural network 808 may be trained with a set of real projection data and a corresponding reconstruction model or reconstruction images. The reconstruction images can be used as the ground truth during training and the real projection data may be used as the input to the deep-learning neural network 808 during training. Training of the deep-learning neural network 808 may then be similar to the training discussed above.

While a deep-learning neural network 808 has a been used in the example system 820 depicted in FIG. 8C, other machine learning techniques or neural networks, such as recurrent or convolutional neural networks, may be used in place of, or in combination with, the deep-learning neural network 808. For example, hidden Markov models or support vector machines may also be used. In general, the machine learning techniques are supervised learning techniques and are trained based on a known set of data, as discussed herein. Those machine learning techniques may be reinforced as additional imaging data is acquired for different patients.

Figure 9A:
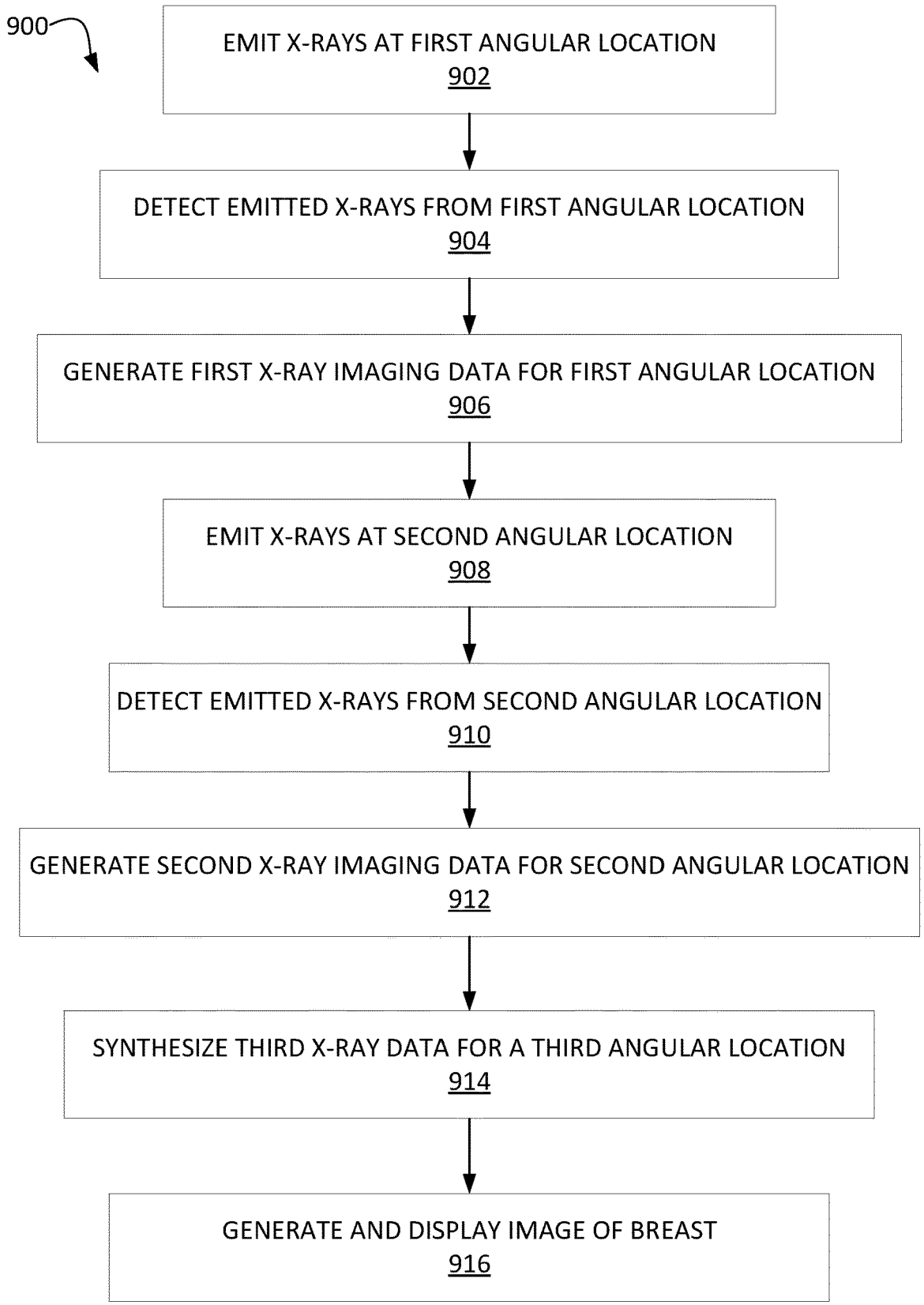
FIG. 9A depicts a method for generating images of a breast.

FIG. 9A depicts a method 900 for generating images of a breast. At operation 902, a first x-ray emission is emitted from an x-ray source at a first angular location. For example, an x-ray source may emit x-rays from the angular location L1. At operation 904, the emitted x-ray emission is detected after passing through the breast from the first angular location. At operation 904, first x-ray imaging data is generated from the first x-ray emission detected at operation 904. The first x-ray imaging data may be a real projection for the first angular location. Operations 902-906 effectively then repeat for a second angular location. For instance, at operation 908, a second x-ray emission is emitted from the second angular location. As an example, the x-ray source may emit x-rays from the angular location L3. At operation 910, the emitted x-ray emission is detected after passing through the breast from the second angular location. At operation 912, second x-ray imaging data is generated from the second x-ray emission detected at operation 910. The second x-ray imaging data may be a real projection for the second angular location.

At operation 914, third x-ray imaging data for a third angular location is synthesized based on at least the first x-ray imaging data and the second x-ray imaging data. The third angular location is different from the first and second angular locations. In the example where the first x-ray imaging data is a real projection for angular location L1 and the second x-ray imaging data is a real projection for angular location L3, the third x-ray imaging data may be a virtual projection for the angular location L2. As such, by generating the third x-ray imaging data for the third angular location without emitting x-ray radiation at the third angular location, the need for an x-ray emission at the third angular location is eliminated. By eliminating the need for the x-ray emission, the overall radiation dose delivered to the patient is reduced and the time required to complete the imaging procedure is reduced.

In another example of method 900, the first x-ray imaging data is a real projection for angular location L5 and the second x-ray imaging data is a real projection for angular location L6. In that example, the third x-ray imaging data generated at operation 914 may be a virtual projection for angular location wider than angular locations L5 and L6, such as angular location L7. As such, by generating the third x-ray imaging data for the third angular location to expand the overall angular range from the angular location of L6 to that of L7, the overall image quality may be improved due to the additional information from the wider angular location of angular location L7. For instance, image artifacts such as overlap structures may be reduced or removed.

Figure 9B:
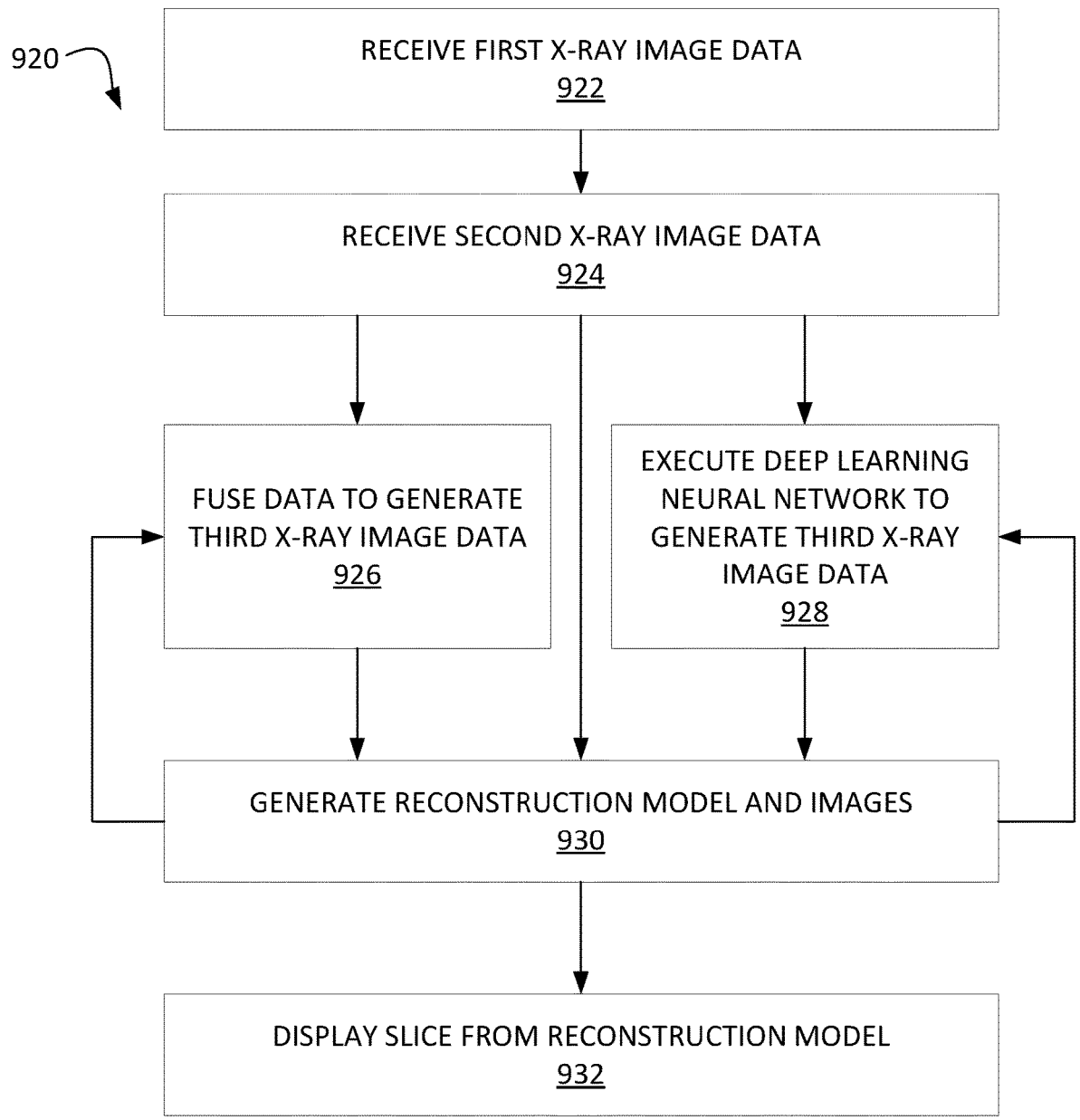
FIG. 9B depicts a method for synthesizing x-ray imaging data.

FIG. 9B depicts a method 920 for synthesizing x-ray imaging data. The method 920 may be used in operation 914 of method 900. At operation 922, first x-ray imaging data for a first angular location is received, and at operation 924, second x-ray imaging data for a second angular location is received. The first x-ray imaging data may be a real projection for a first angular location and the second x-ray imaging data may be a real projection for a second angular location. Third x-ray imaging data for a third angular location, in the form of a virtual projection for example, may then be synthesized at operation 926 and/or operation 928. Synthesizing a virtual projection may include simulating a real projection or other image without the requirement of x-ray emission. At operation 926, the first x-ray imaging data and second x-ray imaging data is fused to create the third x-ray imaging data. Fusing the first x-ray imaging data and second x-ray imaging data may be done by a variety of image analysis and combination techniques, including superposition, interpolation, and extrapolation techniques, among other potential techniques. Interpolation or extrapolation techniques may performed based on the angular locations of the first x-ray imaging data and second x-ray imaging data as compared to the corresponding angular location of the third x-ray imaging data. For instance, where the angular location of the third x-ray imaging data is between the angular locations of the first x-ray imaging data and second x-ray imaging data used to generated the third x-ray imaging data, interpolation techniques may be used. Where the angular location of the third x-ray imaging data is outside the angular locations of the first x-ray imaging data and second x-ray imaging data used to generated the third x-ray imaging data, extrapolation techniques may be used. The techniques for fusing the first x-ray imaging data and second x-ray imaging data to generate the third x-ray imaging data may also be performed in the spatial, transform, or frequency domains. For example, image fusion techniques in the spatial domain generally operate based on the pixel values in the first x-ray imaging data and second x-ray imaging data. Image fusion techniques within the transform or frequency domains generally operate based on mathematical transforms, such as a Fourier or Laplace transform, of the pixel data from the first x-ray imaging data and second x-ray imaging data. For instance, in the frequency domain, the image fusion techniques may be based on a rate of change of pixel values within the spatial domain.

At operation 928, the first x-ray imaging data and second x-ray imaging data are provided as inputs into a trained deep-learning neural network, and the trained deep-learning neural network is executed based on the first x-ray imaging data and second x-ray imaging data to generate the third x-ray imaging data. The trained deep-learning neural network may have been trained based on a set of real projection data, as discussed above and discussed below in further detail with respect to FIG. 9C.

At operation 930, a reconstruction model and/or reconstruction images are generated based on the first x-ray imaging data, the second x-ray imaging data, and the third x-ray imaging data. For example, the first x-ray imaging data and the second x-ray imaging data may be provided to a reconstruction engine. The third x-ray imaging data generating at operation 926 and/or operation 928 may also be provided to the reconstruction engine. The reconstruction engine then generates the reconstruction model and/or reconstruction images based on the first x-ray imaging data, the second x-ray imaging data, and the third x-ray imaging data. In some examples, reconstruction data from the reconstruction model can be provided to a virtual projection synthesizer to be used in operation 926 and/or operation 928 to generate the third x-ray imaging data. In such examples, the reconstruction data is generated at operation 930 based on the first x-ray imaging data and the second x-ray imaging data prior to the generation of the third x-ray imaging data at operation 926 and/or operation 928. In other examples, the process may be iterative, and operation 926 and/or operation 928 may repeat upon receiving the reconstruction data to generate modified third x-ray imaging data. The modified third x-ray imaging data may then be used to generate a modified or updated reconstruction model and/or reconstruction images. At operation 932, one or more reconstruction slices of the breast are displayed based on the reconstruction model and/or reconstruction images generated at operation 930. In other examples, the one or more reconstruction slices of the breast may be displayed concurrently or sequentially with one or more of the acquired real projection images and/or one or more of the generated virtual projection images. In some examples of operation 932, one or more reconstruction slices of the breast, one or more of the acquired real projection images, and/or one or more of the generated virtual projection images may be displayed, either concurrently or sequentially. While the x-ray imaging data in the methods discussed herein are discussed as being first, second, third, etc., such designations are merely for clarity and do necessarily denote any particular order or sequence. In addition, it should be appreciated that additional real x-ray imaging data may be used and more virtual imaging data may also be generated than what is discussed by example in the methods described herein.

Figure 9C:
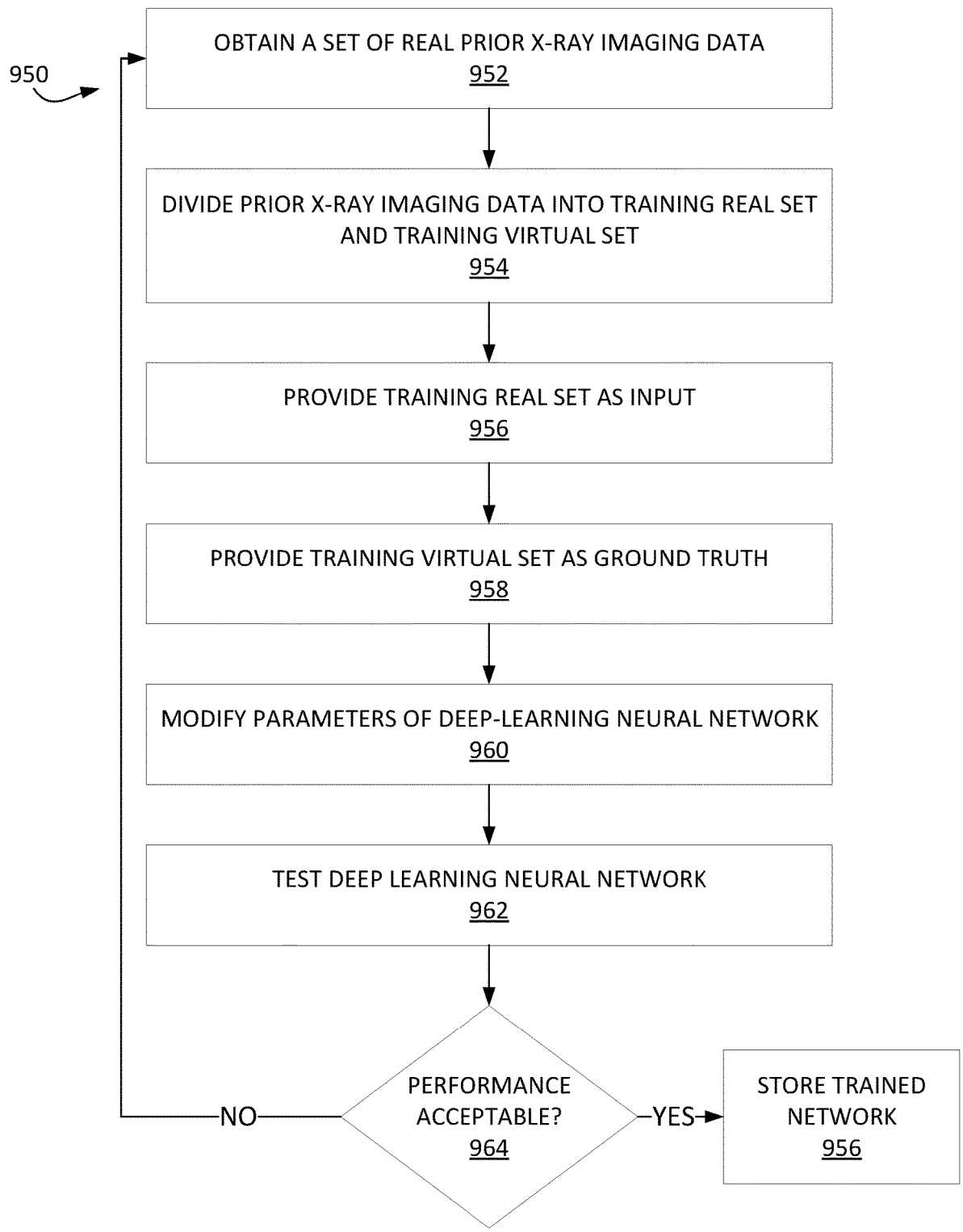
FIG. 9C depicts a method for training a deep-neural network for use in medical imaging.

FIG. 9C depicts a method 950 for training a deep-neural network for use in medical imaging. The method 950 may be used to train the trained deep-learning neural network used in operation 928 of method 920 described above with reference to FIG. 9B. At operation 952, a set of real prior x-ray imaging data used for imaging a breast at multiple angular locations is obtained. The set of real prior x-ray imaging data may be prior tomosynthesis data acquired for a plurality of different breasts. For instance, the real prior x-ray imaging data may be a plurality of real projections taken at different angular locations. At operation 954, the real prior x-ray imaging data is divided into a training real data set for a first plurality of the angular locations and a training virtual data set for a second plurality of the angular locations. The second plurality of angular locations are different from the first plurality of angular locations. As an example, real projection data may be received for angular locations L1, L2, L3, L4, and L5. The real projection data for angular locations L2 and L4 may be divided into a data set of training virtual data. The real projection data is effectively the desired, or ideal, virtual projection data. As such, the deep-learning neural network can be trained to produce virtual projection data based on prior real projection data. The real projection data for angular locations L1, L3, and L5 is left as the training real data set. At operation 956, the training real data set is provided as input to the deep-learning neural network. At operation 958, the training virtual data set is provided to the deep-learning neural network as a ground truth for the training real data set. At operation 960, one or more parameters of the deep-learning neural network are modified based on the training real data set and the training virtual data set. As an example, the coefficients of the deep-learning neural network may be adjusted to minimize a pre-defined cost function that evaluates the difference between the training virtual data set and the output of the deep-learning neural network during training.

At operation 962, the deep-learning neural network is tested. The deep-learning neural network may be tested with other sets of real prior x-ray imaging data to determine the performance and accuracy of the deep-learning neural network. At operation 964, based on the testing performed in operation 962, a determination is made as to whether the performance of the deep-learning neural network is acceptable. The determination may be made based on differences between the output of the deep-learning neural network and the known test data. If the performance is acceptable or within a predetermined tolerance, the trained deep-learning neural network is stored for later use with live real x-ray imaging data. If the performance is not acceptable or outside a predetermined tolerance, the method 950 flows back to operation 952 where the training of the deep-learning neural network continues with an additional set of real prior x-ray imaging data is obtained and used. The method 950 continues and repeats until the deep-learning neural network generates acceptable results that are within the predetermined tolerance.

Figure 10:
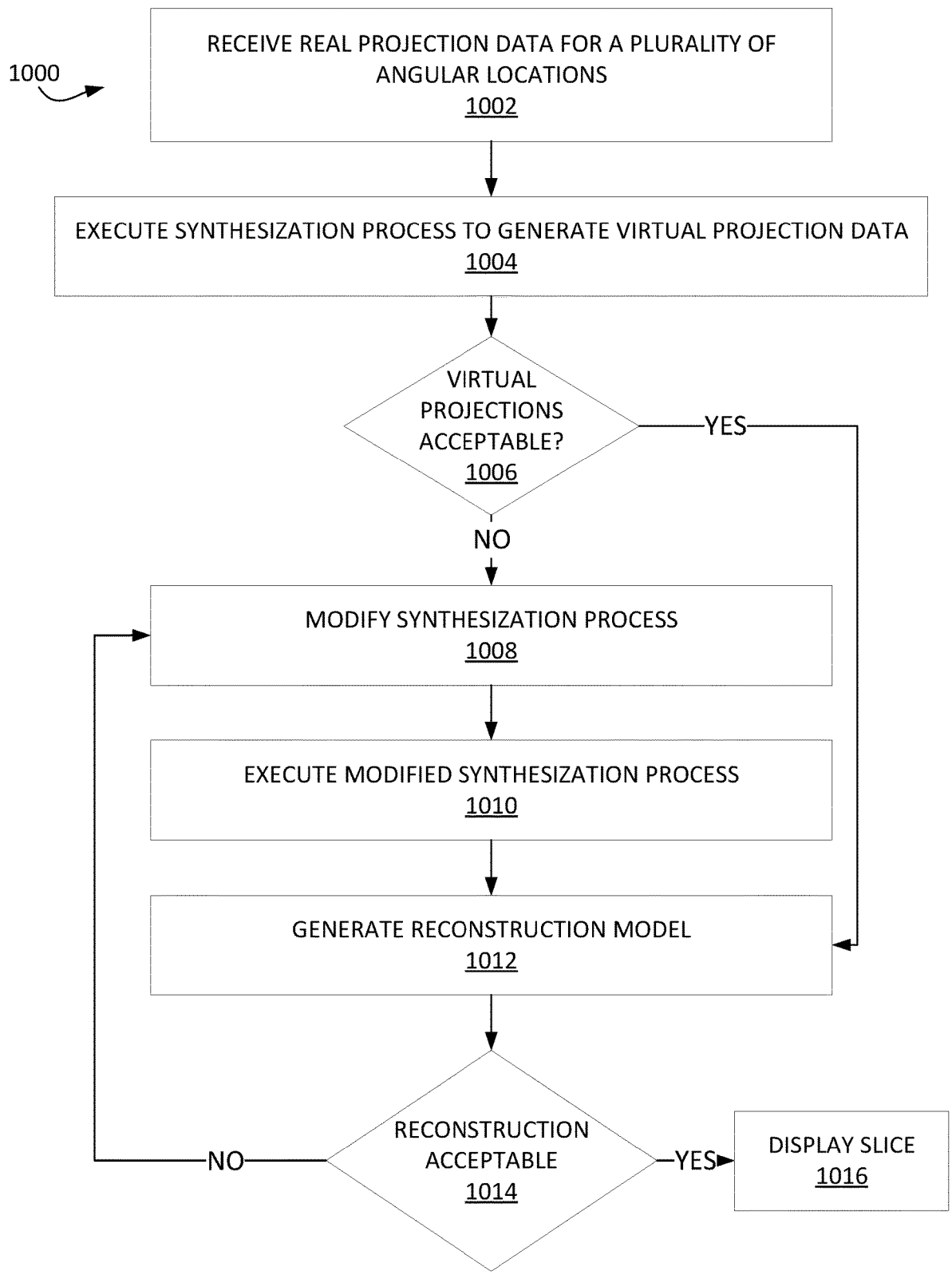
FIG. 10 depicts a method for imaging a breast.

FIG. 10 depicts a method 1000 for imaging a breast. At operation 1002, real projection data is received for a plurality of angular locations. For example, the real projection data may include first real projection data for an x-ray emission from a first angular location relative to the breast, second real projection data for an x-ray emission emitted from a second angular location relative to the breast, and third real projection data for an x-ray emission from a third angular location relative to the breast. At operation 1004, a synthesization process is executed to generate virtual projection data. The synthesization process may include fusing image data and/or executing a trained deep-learning neural network, as discussed above. Continuing with the example above, the synthesization process may generate, based on the first real projection data and the second real projection data, first virtual projection data for an x-ray emission from a fourth angular location relative to the breast, where the fourth angular location is located between the first angular location and the third angular location. The synthesization process may also generate, based on the second real projection data and the third real projection data, second virtual projection data for an x-ray emission from a fifth angular location relative to the breast, where the fifth angular location is located between the second angular location and the fourth angular location.

At operation 1006, a determination is made as to whether the generated virtual projection data is acceptable. For instance, a determination may be made as to whether the image quality of the virtual projection data is within a predetermined tolerance. Continuing with the example above, a determination may be made as to whether at least one of the first virtual projection data or the second virtual projection data has a quality outside of a predetermined tolerance. In one example, determining whether the generated virtual projection data is acceptable is based on the identification of landmarks in the real projection data and the generated virtual projection data. In continuing with the example above, a landmark may be identified in the first real projection data and/or the second real projection data. The landmark may then be identified in the first virtual projection data. The location of the landmark in the first virtual projection data is then compared to the location of the landmark in the first real projection data and/or the second real projection data. Based on the comparison, a determination is made as to whether the location of the landmark in the first virtual projection data is within the predetermined tolerance.

If the virtual projections are determined to be acceptable or within the predetermined tolerance at operation 1006, the method 1000 flows to operation 1012 where a reconstruction model and/or reconstruction images are generated from the real projection data received at operation 1002 and the virtual projection data generated at operation 1004. If, however, the virtual projection data is determined to not be acceptable or outside the predetermined tolerance, the method 1000 flows to operation 1008 where the synthesization process is modified to create a modifying synthesization process. Modifying the synthesization process may include altering the image combination techniques, such as modifying weighting or other parameters, used to combine the real projection data. In examples where the synthesization process includes executing a deep-learning neural network, modifying the synthesization process may include modifying the deep-learning neural network to create a modified deep-learning neural network. Modifying the deep-learning neural network may include adjusting the coefficients of the deep-learning neural network such that the modified deep-learning neural network produces virtual projection data that will fall within the predetermined tolerance.

The modified synthesization process is then executed in operation 1010 to generate modified virtual projection data. In continuing with the example above, the modified synthesization process may be executed to generate a modified first virtual projection and a modified second virtual projection. At operation 1012, a modified reconstruction model and/or modified reconstruction images are generated from the real projection data received at operation 1002 and the modified virtual projection data generated at operation 1010. In continuing with the example above, generating the modified reconstruction model and/or modified reconstruction images may be based on the first real projection data, the second real projection data, the third real projection data, the modified first virtual projection data, and the modified second virtual projection data.

At operation 1014, a determination is made as to whether the reconstruction model and/or reconstruction images generated at operation 1012 are acceptable or within a reconstruction quality tolerance. For example, it may be determined that a particular slice has a quality outside a reconstruction quality tolerance. The determination that the slice has a quality outside a reconstruction quality tolerance may be based on image artifacts within the slice and/or other image quality measurements, such as the sharpness of objects in the slice, contrast-to-noise ratios, spatial resolutions, z-axis resolution or an artifact spread function (e.g., artifact spreading among the slices along the z-direction. If the reconstruction model and/or reconstruction images are determined to be acceptable at operation 1014, the method 1000 flows to operation 1016 where a slice from the reconstruction model and/or reconstruction images is displayed. In other examples, the one or more reconstruction slices of the breast may be displayed concurrently or sequentially with one or more of the acquired real projection images and/or one or more of the generated virtual projection images. In some examples of operation 1016, one or more reconstruction slices of the breast, one or more of the acquired real projection images, and/or one or more of the generated virtual projection images may be displayed, either concurrently or sequentially. If the reconstruction model and/or reconstruction images are determined to not be acceptable at operation 1014, the method 1000 flows back to operation 1008 where the synthesization process may be further modified to create a further modified synthesization process. The further modified synthesization process is then executed at operation 1010 to generate further modified virtual projection data. That further modified virtual projection data may then be used to create a further modified reconstruction model and/or reconstruction images.

Figure 11:
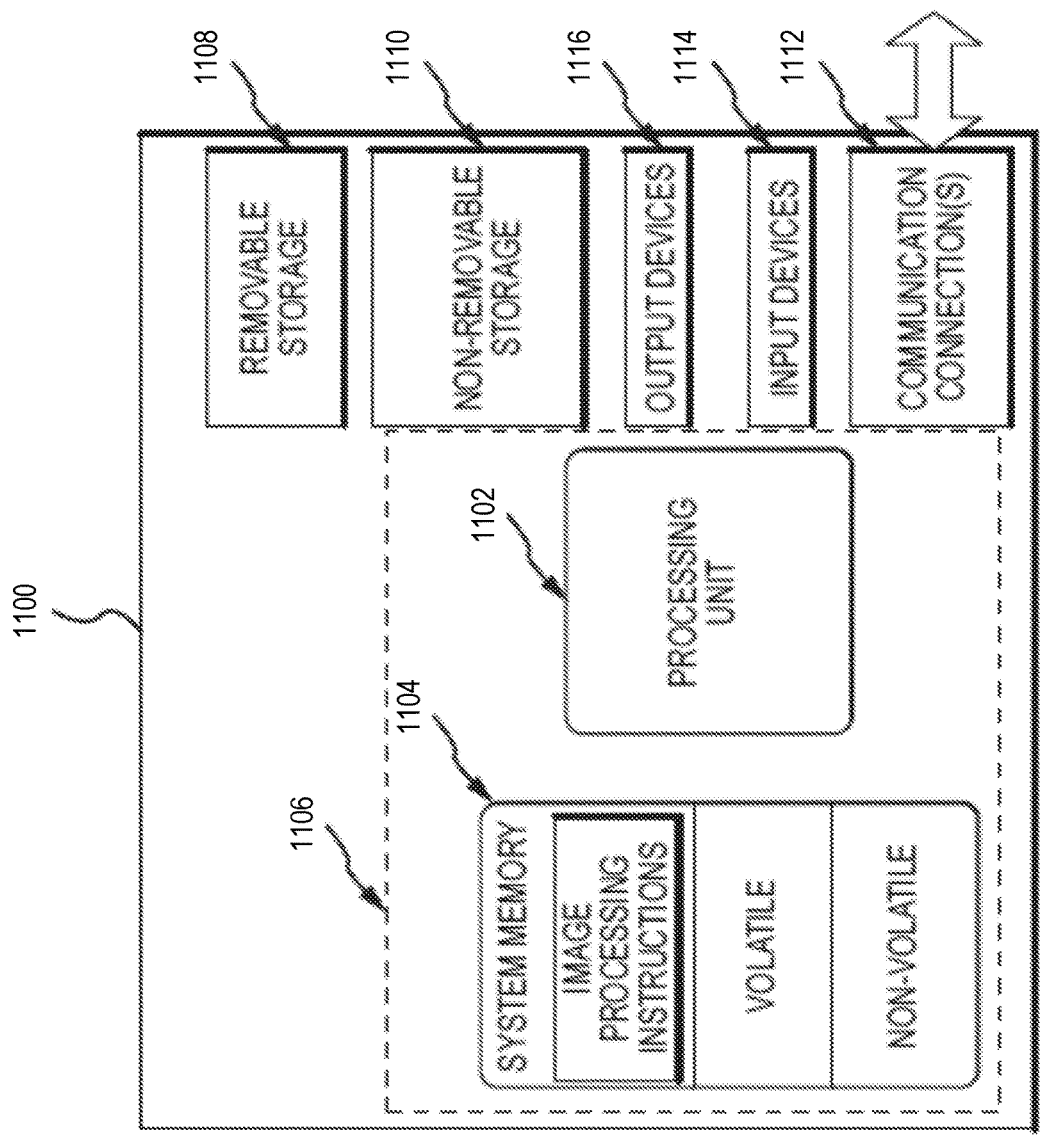
FIG. 11 illustrates one example of a suitable operating environment in which one or more of the present examples can be implemented.

FIG. 11 illustrates one example of a suitable operating environment 1100 in which one or more of the present embodiments can be implemented. This operating environment may be incorporated directly into the imaging systems disclosed herein, or may be incorporated into a computer system discrete from, but used to control, the imaging systems described herein. This is only one example of a suitable operating environment and is not intended to suggest any limitation as to the scope of use or functionality. Other computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 1100 typically includes at least one processing unit 1102 and memory 1104. Depending on the exact configuration and type of computing device, memory 1104 (storing, among other things, instructions to perform the image acquisition and processing methods disclosed herein) can be volatile (such as RAM), non-volatile (such as ROM, flash memory, etc.), or some combination of the two. This most basic configuration is illustrated in FIG. 11 by dashed line 1106. Further, environment 1100 can also include storage devices (removable, 1108, and/or non-removable, 1110) including, but not limited to, magnetic or optical disks or tape. Similarly, environment 1100 can also have input device(s) 1114 such as touch screens, keyboard, mouse, pen, voice input, etc., and/or output device(s) 1116 such as a display, speakers, printer, etc. Also included in the environment can be one or more communication connections 1112, such as LAN, WAN, point to point, Bluetooth, RF, etc.

Operating environment 1100 typically includes at least some form of computer readable media. Computer readable media can be any available media that can be accessed by processing unit 1102 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 1100 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein comprise such modules or instructions executable by computer system 1100 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 1100 is part of a network that stores data in remote storage media for use by the computer system 1100.

Figure 12:
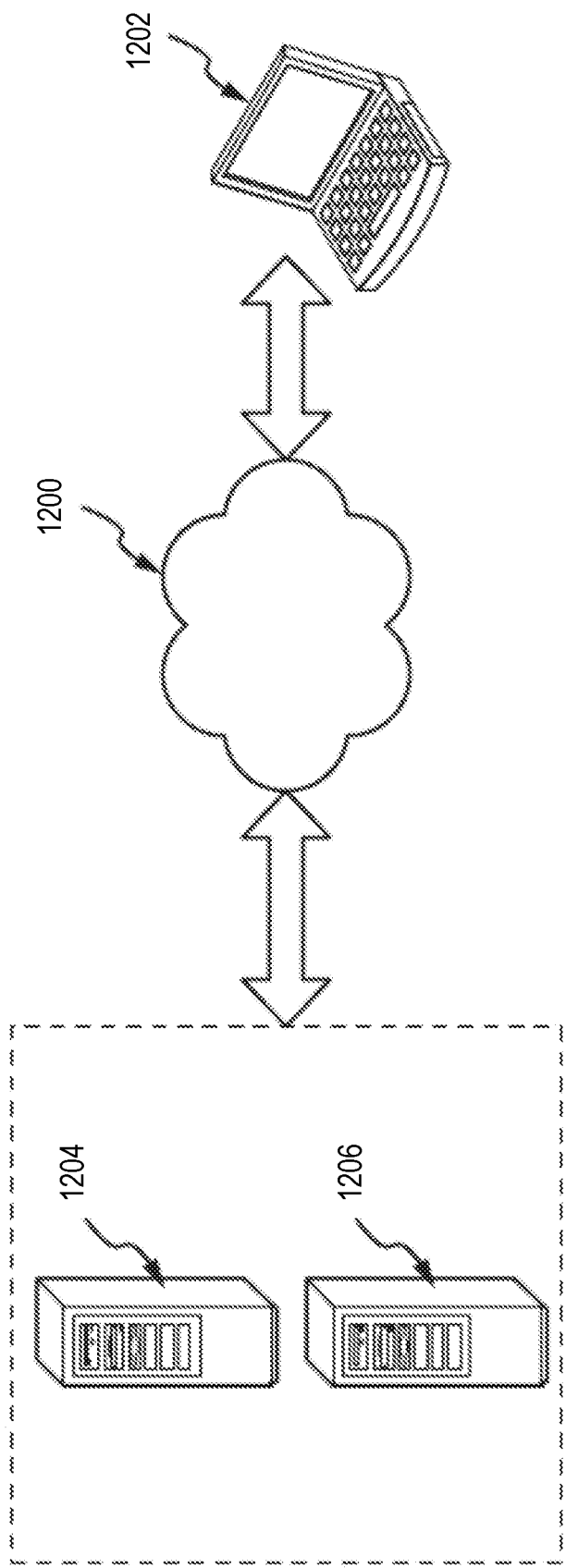
FIG. 12 is an embodiment of a network in which the various systems and methods disclosed herein may operate.

FIG. 12 is an embodiment of a network 1200 in which the various systems and methods disclosed herein may operate. In embodiments, a client device, such as client device 1202, may communicate with one or more servers, such as servers 1204 and 1206, via a network 1208. In embodiments, a client device may be a standalone device may be a portable of fixed work station operatively connected to the acquisition system. The client device may also include or incorporate a laptop, a personal computer, a smart phone, a PDA, a netbook, or any other type of computing device, such as the computing device in FIG. 11. In embodiments, servers 1204 and 1206 may also be any type of computing device, such as the computing device illustrated in FIG. 11. Network 1208 may be any type of network capable of facilitating communications between the client device and one or more servers 1204 and 1206. For example, the surface image data and the internal image data may be acquired locally via the imaging systems and communicated to another computing device(s) for further processing, such as an image acquisition workstation or a cloud-based service. Examples of such networks include, but are not limited to, LANs, WANs, cellular networks, and/or the Internet.

In embodiments, the various systems and methods disclosed herein may be performed by one or more server devices. For example, in one embodiment, a single server, such as server 1204 may be employed to perform the systems and methods disclosed herein, such as the methods for imaging discussed herein. Client device 1202 may interact with server 1204 via network 1208. In further embodiments, the client device 1202 may also perform functionality disclosed herein, such as scanning and image processing, which can then be provided to servers 1204 and/or 1206.

In alternate embodiments, the methods and systems disclosed herein may be performed using a distributed computing network, or a cloud network. In such embodiments, the methods and systems disclosed herein may be performed by two or more servers, such as servers 1204 and 1206. Although a particular network embodiment is disclosed herein, one of skill in the art will appreciate that the systems and methods disclosed herein may be performed using other types of networks and/or network configurations.

In light of the foregoing, it should be appreciated that the present technology is able to reduce the overall radiation does to the patient during an imaging process by acquiring real projection data at fewer angular locations than what was previously used in tomosynthesis procedures. Virtual projections may then be used in place of additional real projections. The combination of the real and virtual projections thus can provide a substantially equivalent reconstruction as that of a former full-dose projection acquisition process. In addition, the present technology can improve the image quality of the reconstructed images, without increasing radiation dosage, by generating virtual projections at angular locations that provide additional information to reduce image artifacts that would otherwise appear in tomosynthesis. Further, the total time required to complete the imaging process is reduced by the present technology. Reducing the time the patient is imaged also reduces the impact of patient movement on the image quality of the reconstructed data.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art. Further, as used herein and in the claims, the phrase "at least one of element A, element B, or element C" is intended to convey any of: element A, element B, element C, elements A and B, elements A and C, elements B and C, and elements A, B, and C.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A system for generating images of a breast, the system comprising:
    an x-ray source;
    an x-ray detector;
    at least one processor operatively connected to the x-ray detector; and
    memory operatively connected to the at least one processor, the memory storing instructions that, when executed by the at least one processor, cause the system to perform a set of operations comprising:
        emitting, from the x-ray source, a first x-ray emission at a first angular location relative to the x-ray detector;
        detecting, by the x-ray detector, the first x-ray emission after passing through the breast;
        generating first x-ray imaging data from the detected first x-ray emission;
        emitting, from the x-ray source, a second x-ray emission at a second angular location relative to the breast;
        detecting, by the x-ray detector, the second x-ray emission after passing through the breast;
        generating second x-ray imaging data from the detected second x-ray emission;
        synthesizing, based on at least the first x-ray imaging data and the second x-ray imaging data, third x-ray imaging data for a third angular location relative to the breast, wherein the third angular location is different from the first angular location and the second angular location, thereby eliminating the need for an x-ray emission at the third angular location, wherein synthesizing the third x-ray imaging data comprises:
            providing the first x-ray imaging data and the second x-ray imaging data into a trained deep-learning neural network; and
            executing the trained deep-learning neural network based on the first x-ray imaging data and the second x-ray imaging data to generate the third x-ray imaging data; and
        generating and displaying an image of the breast from the third x-ray imaging data.

2. The system of claim 1, wherein the first x-ray imaging data is a first real projection for the first angular location, the second x-ray imaging data is a second real projection for the second angular location, and the third x-ray imaging data is a virtual projection for the third angular location.

3. The system of any one of claims 1, wherein synthesizing the third x-ray imaging data includes fusing the first x-ray imaging data and the second x-ray imaging data in at least one of a spatial domain or a frequency domain.

4. The system of any one of claims 1, wherein synthesizing the third x-ray imaging data further comprises:
    generating reconstruction data from the first x-ray imaging data and the second x-ray imaging data; and
    wherein synthesizing the third x-ray imaging data is further based on the generated reconstruction data.

5. The system of claim 1, wherein the operations further comprise training a deep-learning neural network to generate the trained deep-learning neural network, wherein training the deep-learning neural network comprises:
   obtaining a set of real prior x-ray imaging data used for imaging a breast at multiple angular locations;
   dividing the set of real prior x-ray imaging data into a plurality of datasets comprising a training real data set for a first plurality of the angular locations and a training virtual data set for a second plurality of the angular locations, the second plurality of angular locations being different from the first plurality of angular locations;
   providing the training real data set as inputs into the deep-learning neural network; and
   providing the training virtual data set as a ground truth for the deep-learning neural network.

6. The system of any one of claims 1, wherein the operations are performed as part of digital breast tomosynthesis or multi-modality imaging.

7. A computer-implemented method, executed by at least one processor, for generating images of a breast, the method comprising:
   receiving first real projection data for an x-ray emission from a first angular location relative to the breast;
   receiving second real projection data for an x-ray emission emitted from a second angular location relative to the breast;
   receiving third real projection data for an x-ray emission from a third angular location relative to the breast;
   executing a synthesization process to:
      generate, based on the first real projection data and the second real projection data, first virtual projection data for an x-ray emission from a fourth angular location relative to the breast, wherein the fourth angular location is different from the first angular location and the third angular location; and
      generate, based on the second real projection data and the third real projection data, second virtual projection data for an x-ray emission from a fifth angular location relative to the breast, wherein the fifth angular location different from the second angular location and the fourth angular location;
   determining that at least one of the first virtual projection data or the second virtual projection data has a quality outside of a predetermined tolerance;
   based on the determination that the at least one of the first virtual projection or the second virtual projection has a quality outside of a predetermined tolerance, modifying the synthesization process to create a modified synthesization process;
   executing the modified synthesization process to generate a modified first virtual projection and a modified second virtual projection;
   generating a reconstruction model from the first real projection data, the second real projection data, the third real projection data, the modified first virtual projection data, and the modified second virtual projection data; and
   displaying at least one of a slice of the breast from the generated reconstruction model, the first real projection data, the second real projection data, the third real projection data, the first virtual projection data, or the second virtual projection data.

8. The method of claim 7, wherein determining that at least one of the first virtual projection data or the second virtual projection data has a quality outside of a predetermined tolerance further comprises:
   identifying a landmark in one of the first real projection data or the second real projection data;
   identifying the landmark in the first virtual projection data;
   comparing the location of the landmark in the first virtual projection data to the location of the landmark in at least one of the first real projection data or the second real projection data; and
   based on the comparison, determining whether the location of the landmark in the first virtual projection data is within the predetermined tolerance.

9. The method of any one of claims 7, wherein the synthesization process comprises:
   providing the first real projection data, the second real projection data, the third real projection data into a trained deep-learning neural network; and
   executing the trained deep-learning neural network based on the first real projection data, the second real projection data, the third real projection data to generate the first virtual projection data and the second virtual projection data.

10. The method of claim 9, wherein modifying the synthesization process comprises modifying coefficients of the trained deep-learning neural network.

11. The method of any one of claims 7, further comprising:
   determining that the slice has a quality outside a reconstruction quality tolerance; and
   based on the determination that the slice has a quality outside a reconstruction quality tolerance, further modifying the modified synthesization process to create a further modified synthesization process.

12. The method of claim 11, further comprising:
   executing the further modified synthesization process to generate a further modified first virtual projection data and a further modified second virtual projection data;
   generating a modified reconstruction model from the first real projection data, the second real projection data, the third real projection data, the further modified first virtual projection data, and the further modified second virtual projection data; and
   displaying at least one of a slice of the breast from the modified reconstruction model, the further modified first virtual projection, or the further modified second virtual projection.

13. The method of any one of claims 7, wherein the method is performed as part of digital breast tomosynthesis or multi-modality imaging.

14. A computer-implemented method, executed by at least one processor, for generating images of a breast, the method comprising:
   receiving first real projection data for an x-ray emission from a first angular location relative to the breast;
   receiving second real projection data for an x-ray emission emitted from a second angular location relative to the breast;
   providing the first real projection data and the second real projection data into a trained deep-learning neural network;
   executing the trained deep-learning neural network based on the first real projection data, and the second real projection data to generate first virtual projection data for a third angular location relative to the breast;

generating a reconstruction model from the first real projection data, the second real projection data, and the first virtual projection data; and displaying at least one of a slice of the breast from the generated reconstruction model, the first real projection data, the second real projection data, or the first virtual projection data.

15. The method of claim 14, further comprising:

determining that the slice has a quality outside a reconstruction quality tolerance; and based on the determination that the slice has a quality outside a reconstruction quality tolerance, modifying the trained deep-learning neural network to create a modified deep-learning neural network.

16. The method of claim 15, further comprising:

executing the modified deep-learning neural network based on the first real projection data and the second real projection data to generate a modified first virtual projection;

generating a modified reconstruction model from the first real projection data, the second real projection data, and the modified first virtual projection data; and displaying at least one of a slice of the breast from the modified reconstruction model or the modified first virtual projection.

17. The method of any one of claims 15, wherein the determination that the slice has a quality outside a reconstruction quality tolerance is based on at least one of image artifacts or image quality measurements.

18. The method of one of claims 14, wherein the difference between the first angular location and the second angular location is less than or equal to three degrees.

19. The method of any one of claims 14, wherein the method is performed as part of digital breast tomosynthesis or multi-modality imaging.

* * * * *